(12) United States Patent
Renz et al.

(10) Patent No.: US 7,776,008 B2
(45) Date of Patent: Aug. 17, 2010

(54) MANUAL BREAST PUMP

(75) Inventors: Charles J. Renz, Briarcliff Manor, NY (US); Daniel J. Nelsen, Providence, RI (US); David Robson, Riverside, RI (US); Aidan Petrie, Jamestown, RI (US)

(73) Assignee: Playtex Products, Inc., Westport, CT (US)

( * ) Notice: Subject to any disclaimer, the term of this patent is extended or adjusted under 35 U.S.C. 154(b) by 3 days.

(21) Appl. No.: 10/982,963

(22) Filed: Nov. 5, 2004

(65) Prior Publication Data

US 2005/0154349 A1    Jul. 14, 2005

Related U.S. Application Data

(63) Continuation-in-part of application No. 10/637,979, filed on Aug. 8, 2003.

(51) Int. Cl.
 *A61M 1/06* (2006.01)
(52) U.S. Cl. ....................................................... 604/74
(58) Field of Classification Search .............. 604/74–76
 See application file for complete search history.

(56) References Cited

U.S. PATENT DOCUMENTS

| | | | |
|---|---|---|---|
| 11,135 A | 6/1854 | Needham | |
| 2,160,651 A | 5/1939 | Erling | 31/69 |
| 2,419,795 A | 4/1947 | Saunders | 128/297 |
| 2,542,505 A | 2/1951 | Gascoigne | 128/281 |
| 2,584,435 A | 2/1952 | Doerr | 257/10 |
| 2,612,136 A | 9/1952 | Davis | 119/14.52 |
| 2,696,193 A | 12/1954 | Domingo | 119/14.01 |
| 2,809,607 A | 10/1957 | Golay | 119/14.41 |
| 3,382,867 A | 5/1968 | Reaves | 128/38 |
| 3,620,408 A | 11/1971 | Holbrook et al. | 220/60 |
| 3,699,815 A | 10/1972 | Holbrook | 73/427 |
| 3,738,363 A | 6/1973 | Lunas et al. | 128/281 |
| 3,741,161 A | 6/1973 | Zhuk et al. | 119/14.36 |
| 3,782,385 A | 1/1974 | Loyd | 128/281 |
| 3,911,920 A | 10/1975 | Susinn | 128/281 |
| 3,977,405 A | 8/1976 | Yanase | 128/281 |
| 4,041,904 A | 8/1977 | Yang | 119/14.41 |

(Continued)

FOREIGN PATENT DOCUMENTS

DE    2807646    8/1978

(Continued)

OTHER PUBLICATIONS

UK Office Action dated Nov. 26, 2008 from UK Patent Application No. 0708814.9.

(Continued)

*Primary Examiner*—Kevin C Sirmons
*Assistant Examiner*—Catherine N Witczak
(74) *Attorney, Agent, or Firm*—Ohlandt, Greeley, Ruggiero & Perle, L.L.P.

(57) ABSTRACT

A manually actuated breast pump is provided. The breast pump has a breast cup, pump mechanism and a container. The components of the breast pump are easily assembled and disassembled to facilitate use, cleaning, manufacture and transport. The breast pump can apply a negative pressure, a positive pressure or both to a user's breast. The breast pump provides fluid isolation between the pressure source and the expressed milk.

2 Claims, 17 Drawing Sheets

U.S. PATENT DOCUMENTS

| | | | |
|---|---|---|---|
| D251,015 S | 2/1979 | Cone | D24/23 |
| 4,249,481 A | 2/1981 | Adams | 119/14.02 |
| 4,263,912 A | 4/1981 | Adams | 128/281 |
| 4,280,445 A | 7/1981 | Phillips | 119/14.02 |
| 4,311,141 A | 1/1982 | Diamond | 128/281 |
| 4,323,067 A | 4/1982 | Adams | 128/281 |
| 4,501,585 A | 2/1985 | Friedman | 604/346 |
| 4,573,969 A | 3/1986 | Schlensog et al. | 604/74 |
| 4,583,970 A | 4/1986 | Kirchner | 604/74 |
| D283,732 S | 5/1986 | Elliott | D24/23 |
| 4,607,596 A | 8/1986 | Whittlestone et al. | 119/14.02 |
| 4,673,388 A | 6/1987 | Schlensog et al. | 604/74 |
| 4,680,028 A | 7/1987 | Stuart | 604/74 |
| 4,740,196 A | 4/1988 | Powell | 604/75 |
| 4,754,776 A | 7/1988 | McKee | 137/102 |
| 4,759,747 A | 7/1988 | Aida et al. | 604/74 |
| 4,761,160 A | 8/1988 | Vermillion | 604/76 |
| 4,772,262 A | 9/1988 | Grant et al. | 604/74 |
| 4,774,874 A | 10/1988 | Adahan | 92/59 |
| 4,796,758 A | 1/1989 | Hauk | 206/545 |
| 4,799,922 A | 1/1989 | Beer et al. | 604/74 |
| 4,813,932 A | 3/1989 | Hobbs | 604/74 |
| 4,857,051 A | 8/1989 | Larsson | 604/74 |
| 4,883,464 A | 11/1989 | Morifuki | 604/74 |
| 4,886,494 A | 12/1989 | Morifuji | 604/74 |
| 4,892,517 A | 1/1990 | Yuan et al. | 604/74 |
| 4,929,229 A | 5/1990 | Larsson | 604/74 |
| D309,500 S | 7/1990 | Yuan et al. | D24/51 |
| 4,950,236 A | 8/1990 | Wilson | 604/74 |
| 4,961,726 A | 10/1990 | Richter | 604/74 |
| 4,964,851 A | 10/1990 | Larsson | 604/74 |
| D313,103 S | 12/1990 | Kawano | D24/51 |
| 5,007,899 A | 4/1991 | Larsson | 604/74 |
| 5,009,638 A | 4/1991 | Riedweg et al. | 604/74 |
| 5,049,126 A | 9/1991 | Larsson | 604/74 |
| 5,071,403 A | 12/1991 | Larsson | 604/74 |
| 5,100,406 A | 3/1992 | Panchula | 606/74 |
| 5,161,482 A | 11/1992 | Griffin | 119/14.02 |
| 5,178,095 A | 1/1993 | Mein | 119/14.47 |
| D345,209 S | 3/1994 | Shoda et al. | D24/109 |
| 5,295,957 A | 3/1994 | Aida et al. | 604/74 |
| 5,304,129 A | 4/1994 | Forgach | 604/74 |
| 5,308,321 A | 5/1994 | Castro | 604/74 |
| 5,358,476 A | 10/1994 | Wilson | 604/74 |
| 5,415,632 A | 5/1995 | Samson | 604/74 |
| 5,474,193 A | 12/1995 | Larsson et al. | 215/11.4 |
| 5,514,166 A | 5/1996 | Silver et al. | 604/74 |
| D372,975 S | 8/1996 | Meyers et al. | D24/109 |
| 5,542,921 A | 8/1996 | Meyers et al. | 604/74 |
| D375,357 S | 11/1996 | Silver | D24/129 |
| 5,571,084 A | 11/1996 | Palmer | 604/74 |
| 5,575,768 A | 11/1996 | Lockridge et al. | 604/74 |
| 5,601,531 A | 2/1997 | Silver | 604/74 |
| 5,616,125 A | 4/1997 | Jelks | 604/74 |
| D383,536 S | 9/1997 | Bachman et al. | D24/109 |
| 5,720,722 A | 2/1998 | Lockridge | 604/74 |
| 5,749,850 A | 5/1998 | Williams et al. | 604/74 |
| 5,776,098 A | 7/1998 | Silver et al. | 604/74 |
| 5,797,875 A | 8/1998 | Silver | 604/74 |
| 5,810,772 A | 9/1998 | Niederberger | 604/74 |
| 5,843,029 A | 12/1998 | Bachman et al. | 604/74 |
| 5,871,456 A | 2/1999 | Armstrong et al. | 601/14 |
| 5,885,246 A | 3/1999 | Ford | 604/74 |
| D408,528 S | 4/1999 | Kan | D24/109 |
| 5,897,580 A | 4/1999 | Silver | 607/108 |
| 5,902,267 A | 5/1999 | Medo | 604/74 |
| 5,941,847 A | 8/1999 | Huber et al. | 604/74 |
| 5,947,923 A | 9/1999 | Uehara et al. | 604/74 |
| 5,954,690 A | 9/1999 | Larsson | 604/74 |
| 5,971,952 A | 10/1999 | Medo | 604/74 |
| 5,992,347 A | 11/1999 | Innings et al. | 119/14.07 |
| 6,004,186 A | 12/1999 | Penny | 450/36 |
| 6,004,288 A | 12/1999 | Hochstedler et al. | 604/74 |
| D418,598 S | 1/2000 | Jauch | D24/109 |
| D420,443 S | 2/2000 | Morifuji | D24/109 |
| 6,042,560 A | 3/2000 | Niederberger | 604/74 |
| 6,045,529 A | 4/2000 | Nüesch | 604/74 |
| 6,050,432 A | 4/2000 | Koehnke | 215/11.3 |
| 6,056,730 A | 5/2000 | Greter | 604/319 |
| 6,090,065 A | 7/2000 | Giles | 604/74 |
| 6,093,168 A | 7/2000 | Mendenhall | 604/74 |
| 6,109,100 A | 8/2000 | Buckley et al. | 73/198 |
| 6,110,140 A | 8/2000 | Silver | 604/74 |
| 6,110,141 A | 8/2000 | Nüesch | 604/74 |
| 6,139,521 A | 10/2000 | Larsson | 604/74 |
| 6,149,395 A | 11/2000 | Richter | 417/182 |
| 6,152,896 A | 11/2000 | Bachman et al. | 604/74 |
| 6,210,360 B1 | 4/2001 | Kong | 604/73 |
| 6,213,840 B1 | 4/2001 | Han | 450/36 |
| 6,227,936 B1 | 5/2001 | Mendoza | 450/36 |
| 6,257,847 B1 | 7/2001 | Silver et al. | 417/415 |
| D446,300 S | 8/2001 | Kirchner | D24/109 |
| D446,852 S | 8/2001 | Johansen et al. | D24/109 |
| D446,853 S | 8/2001 | Johansen et al. | D24/109 |
| 6,270,474 B1 | 8/2001 | Nüesch | 604/74 |
| 6,273,868 B1 | 8/2001 | Nordvik | 604/74 |
| 6,287,521 B1 | 9/2001 | Quay et al. | 422/101 |
| 6,290,671 B1 | 9/2001 | Niederberger | 604/74 |
| 6,299,594 B1 | 10/2001 | Silver | 604/74 |
| 6,328,082 B1 | 12/2001 | Lafond | 141/313 |
| 6,355,012 B1 | 3/2002 | Nüesch | 604/74 |
| 6,358,226 B1 | 3/2002 | Ryan | 604/74 |
| 6,379,327 B2 | 4/2002 | Lundy | 604/74 |
| 6,383,163 B1 | 5/2002 | Kelly et al. | 604/74 |
| 6,383,164 B1 | 5/2002 | Johansen et al. | 604/74 |
| 6,387,072 B1 | 5/2002 | Larsson et al. | 604/74 |
| 6,423,030 B1 | 7/2002 | Silver | 604/74 |
| 6,440,100 B1 | 8/2002 | Prentiss | 604/74 |
| 6,461,324 B1 * | 10/2002 | Schlensog | 604/74 |
| 6,481,986 B1 | 11/2002 | Silver et al. | 417/441 |
| 6,497,677 B2 * | 12/2002 | Silver | 604/74 |
| 6,500,143 B2 | 12/2002 | Suh | 604/73 |
| 6,517,513 B1 | 2/2003 | Covington et al. | 604/74 |
| 6,547,756 B1 | 4/2003 | Greter et al. | 604/74 |
| 6,579,258 B1 | 6/2003 | Atkin et al. | 604/74 |
| 6,585,686 B2 | 7/2003 | Cloud | 604/74 |
| 6,887,210 B2 * | 5/2005 | Quay | 600/573 |
| 6,974,440 B2 * | 12/2005 | Silver | 604/74 |
| 2001/0016708 A1 | 8/2001 | Kong et al. | 604/152 |
| 2001/0038799 A1 | 11/2001 | Silver et al. | 417/515 |
| 2001/0044593 A1 | 11/2001 | Lundy | 604/74 |
| 2001/0047148 A1 | 11/2001 | Suh | 604/74 |
| 2002/0004642 A1 | 1/2002 | Cloud | 604/74 |
| 2002/0032404 A1 | 3/2002 | Silver | 604/74 |
| 2002/0033199 A1 | 3/2002 | Lafond | 141/10 |
| 2002/0072701 A1 | 6/2002 | Nuesch | 604/74 |
| 2002/0072702 A1 | 6/2002 | Quay | 604/74 |
| 2002/0127580 A1 | 9/2002 | Quay | 435/6 |
| 2002/0156419 A1 | 10/2002 | Silver et al. | 604/74 |
| 2002/0170935 A1 | 11/2002 | Annis | 224/653 |
| 2002/0193731 A1 | 12/2002 | Myers et al. | 604/74 |
| 2002/0198489 A1 | 12/2002 | Silver et al. | 604/74 |
| 2003/0004459 A1 | 1/2003 | McKendry et al. | 604/74 |
| 2003/0040734 A1 | 2/2003 | Morton et al. | 604/514 |
| 2003/0069536 A1 | 4/2003 | Greter et al. | 604/74 |
| 2003/0073951 A1 | 4/2003 | Morton et al. | 604/73 |
| 2003/0149398 A1 | 8/2003 | Renz et al. | 604/74 |
| 2003/0150890 A1 | 8/2003 | Perricone | 224/148.6 |
| 2003/0191432 A1 | 10/2003 | Silver | 604/74 |
| 2003/0191433 A1 | 10/2003 | Prentiss | 604/74 |
| 2003/0204164 A1 | 10/2003 | Britto et al. | 604/74 |
| 2004/0015127 A1 * | 1/2004 | Silver et al. | 604/74 |
| 2004/0039330 A1 | 2/2004 | Silver | 604/74 |
| 2004/0087898 A1 * | 5/2004 | Weniger | 604/74 |

| | | | |
|---|---|---|---|
| 2005/0234370 A1 | 10/2005 | Beal et al. | |
| 2005/0256449 A1* | 11/2005 | Tashiro | 604/74 |

FOREIGN PATENT DOCUMENTS

| | | |
|---|---|---|
| DE | 3047440 | 12/1980 |
| EP | 0198469 | 10/1986 |
| EP | 0466462 | 1/1992 |
| GB | 185521 | 9/1922 |
| GB | 2127293 | 4/1984 |
| GB | 2138686 | 10/1984 |
| GB | 2420504 A | 5/2006 |
| JP | 6292720 A | 10/1994 |
| WO | WO97/05913 | 2/1997 |
| WO | WO 99/44650 | 9/1999 |
| WO | WO 02/26290 | 4/2002 |
| WO | WO 02/38032 | 5/2002 |
| WO | WO 2003/057277 | 7/2003 |
| WO | WO2005016409 A2 | 2/2005 |

OTHER PUBLICATIONS

International Search Report based on PCT US07/08782, dated Sep. 12, 2008.
Written Opinion based on PCT US07/08782, dated Sep. 12, 2008.
Combined Search and Examination Report dated Jul. 2, 2009 for corresponding British patent application No. GB0909240.4.
Combined Search and Examination Report dated Jul. 2, 2009 for corresponding British patent application No. GB0909241.2.

* cited by examiner

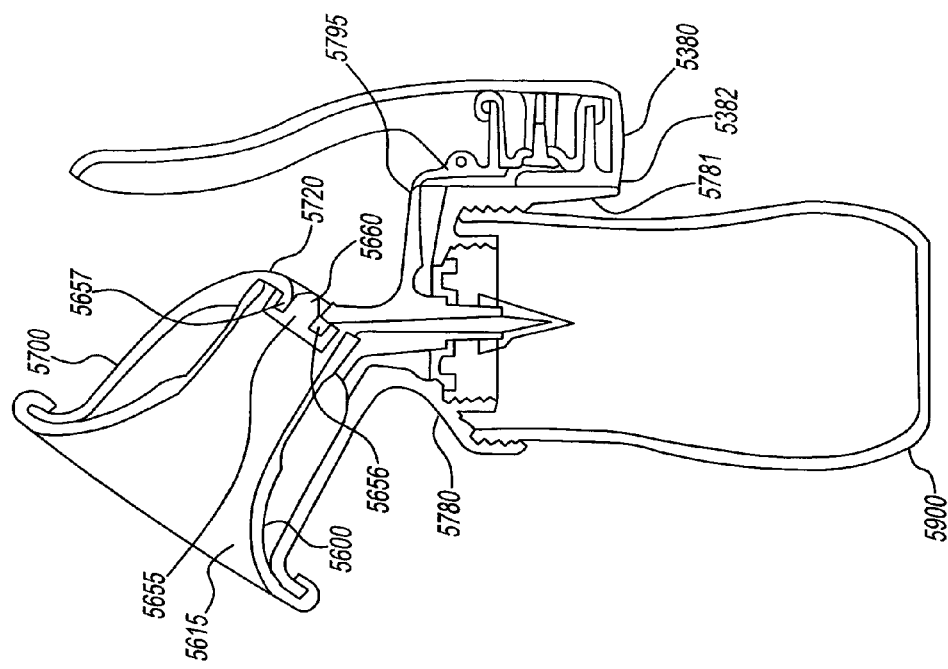
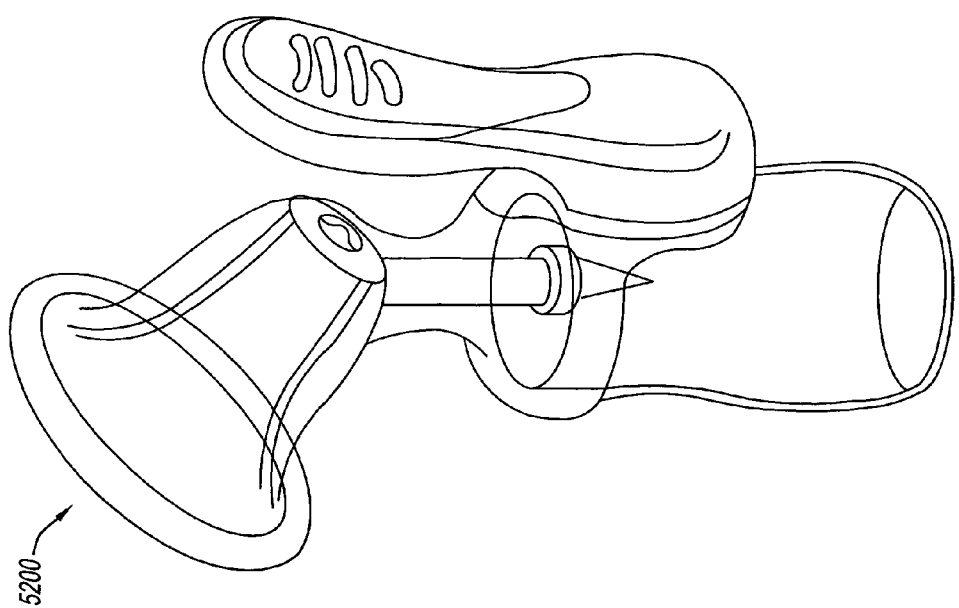

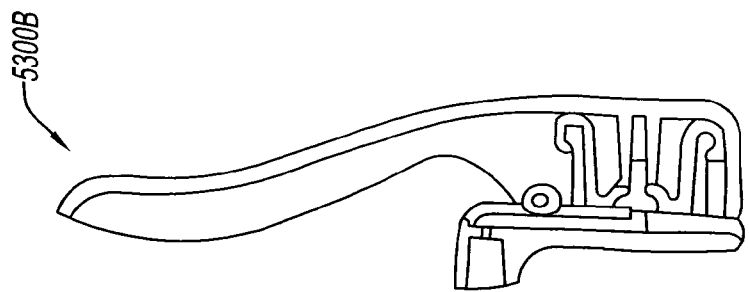
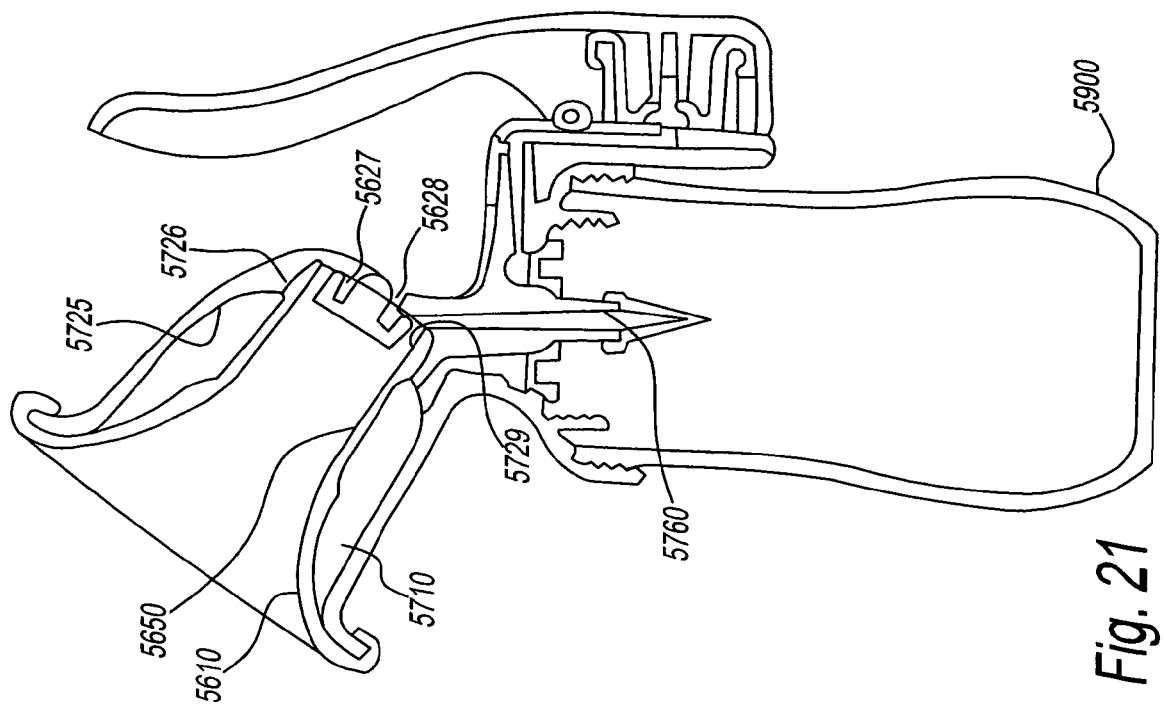

MANUAL BREAST PUMP

RELATED APPLICATION

This application is a continuation-in-part of copending U.S. application Ser. No. 10/637,979, filed Aug. 8, 2003, the disclosure of which is incorporated by reference herein in its entirety.

BACKGROUND OF THE INVENTION

1. Field of the Invention

The present invention relates to devices and methods to obtain breast milk. More particularly, the present invention relates to a device and method for expressing breast milk through use of a breast cup and manual pump.

2. Description of the Related Art

Breast pump systems that use either manual or automatic means for obtaining breast milk are known in the art. Typically, these systems use a vacuum source to generate a negative pressure through a hood or cup that is applied to the breast. Contemporary automated breast pumps typically use separate breast receiving portions and pump mechanisms by applying the vacuum pressure through tubing or conduit connected therebetween.

Conventional devices suffer from several drawbacks. These devices often apply only a negative pressure and apply such negative pressure from the base of the breast cup. This is an inaccurate and inefficient simulation of the way a suckling baby feeds. A baby often applies pressure all around the nipple area of the breast, and from different directions. A baby often applies a positive massaging pressure as well, which helps stimulate the release of milk from the milk ducts.

Some of these devices function by having the user remove the pump from her breast after each cycle of the vacuum device to expose the breast cup to ambient air pressure. This is done because such devices need the pressure inside the breast cup to be reset before it can apply an effective negative pressure through suction.

Many contemporary devices also do not separate the air in the vacuum system from the air in the breast cup. This potentially would allow the milk to enter the pump mechanism, causing damage to the system and unwanted cleanup.

The contemporary manual pump systems have pump handles that are not ergonomically designed to fit a woman's hand. The handles slope away from the breast cup and require the woman to extend her hand in an uncomfortable manner. Over repeated cycles of pumping, such designs can result in prolonged pain to the user's hand. Contemporary manual pumps often require that the pump mechanism be connected to the breast cup, which may be uncomfortable and tiresome for the user. Contemporary manual breast pump systems further fail to facilitate cleaning of the devices through use of easily separable components.

SUMMARY OF THE INVENTION

An object of the present invention is to provide a breast pump for applying a positive massaging pressure to the breast, as well as the negative vacuum pressure to express breast milk.

Another object of the present invention is to provide the breast pump with a barrier or isolation member that separates the breast from the vacuum system, thereby reducing or eliminating the risk of contamination of the breast milk.

A further object of the present invention is to provide the user of the breast pump with handles that increase comfort when using the breast pump.

A still further object of the present invention is to provide an inverted manual pump handle that is better suited to the characteristics of a female user's hand.

A still yet further object of the present invention is to provide a breast pump with ergonomic pump handles that are connectable to the breast cup or by manual pump handles that can be used remotely from the cup and that create a vacuum in the cup through tubing attached to the cup.

These and other objects and advantages of the present invention are achieved by a breast pump that has a breast cup, a pump mechanism and a container. The breast cup directly contacts the breast. The pump mechanism utilizes one of several manually actuated processes to apply positive and/or negative pressure to the breast through the breast cup. The container is a depository for the expressed milk.

The breast cup has a housing, a flexible insert sealingly secured to the housing to form a vacuum air volume (air volume), an air and liquid volume that are in contact with the user's breast (liquid volume), and an air orifice in fluid communication with the air volume and in fluid isolation from the liquid volume. The air volume and liquid volume are in fluid isolation, and the air volume contracts or expands as negative or positive pressure is applied. The housing can have an air orifice that is in fluid communication with the air volume and in fluid isolation from the liquid volume.

The insert is secured to the housing so that there exists an air volume between the insert and the housing. The flexible insert thus isolates the fluid volume from the air volume.

The flexible insert can have a bladder and the air volume can be at least partially in the bladder. The bladder moves in response to a change in pressure in the air volume. The flexible insert can also have a second portion with a circumferential wall and two or more spacers formed in the circumferential wall with the circumferential wall being separated from the housing by the spacers. The circumferential wall and the spacers at least partially define the air volume, and the circumferential wall is moved in relation to the housing by the change in pressure in the air volume.

The breast cup can also have a barrier member disposed substantially adjacent to the bladder with the barrier member preventing the breast from contacting the bladder. The barrier member can have a cylindrical shape and is in the liquid volume.

The flexible insert can have a funnel shape with a first portion that at least partially defines the air volume and a massaging projection formed on the first portion. The massaging projection can be along the first portion in proximity to the areola region of the breast. The massaging projection can have a star-like shape.

The housing can have a first end and a second end. The insert can have a third end and a fourth end. The first end can be removably secured to the second end by a first securing structure, and the third end can be removably secured to the fourth end by a second securing structure. The first securing structure and the second securing structure can be tongue and groove securing structures. The air volume can have a maximum capacity for expansion, and the maximum capacity for expansion can be an upper limit for the positive pressure.

The housing, the insert and the holder can be securable to each other at any rotational orientation. The holder can be secured to the housing by a snap fit connection. The expressed milk passes through the fluid volume in the flexible insert, through a one-way valve that is connected to the holder, and into the container. The container can be a first container having a first diameter and a second container having a second diameter. The holder can have a first securing structure and a second securing structure, with the first securing structure being removably securable to the first container and the second securing structure being removably securable to the second container. The first securing structure can be a first threaded surface having a first inner diameter and the second securing structure can be a second threaded surface having a second inner diameter. The first threaded surface and the second threaded can be concentrically disposed on the holder.

The present invention also has a breast cup that reduces the number of components to two, namely a flexible insert and a holder. In these embodiments, the user places the insert into the upper opening of the holder and seals it to the base of the holder. The separate air and fluid volumes are maintained by sealing the upper part of the insert around the upper edges of the holder and by securing the base of the insert to a structure on the holder. This embodiment also includes variations in which the user is required to secure the insert in the holder by pulling it into the base of the holder with a device located behind the base, or where the insert is press-fitted into a securing structure in the base. This variation also maintains the separate air and liquid volumes.

The pump mechanism is connected to the holder so that the air volume that is isolated between the flexible insert, and the holder is in fluid communication with a chamber where positive and negative pressures are created by the pump mechanism. The pressure chamber can be located externally adjacent to the container. The preferred embodiment of the pump mechanism is a diaphragm that is connected to a handle that the user manipulates to expand or contract the diaphragm, to create positive or negative pressure in the chamber and, consequently, the air volume and flexible insert. However, the present invention also includes any method in which air in a chamber is moved with a manual device to create positive or negative pressure on the isolated air volume located between the flexible insert and the holder.

The handle to be manipulated by the user extends upward from the chamber, providing an easy way for the user to grip the handle. The handle is pulled toward the breast cup and released to create negative and positive pressure in the chamber. The body of the handle can be made of a stiff plastic to provide support, and the grip can be made from a softer plastic for an easier grip.

The pump mechanism can also be removed from the container and holder, for purposes of cleaning or maintenance. In this variation, the pump mechanism would have a way for the chamber to be sealed again when the mechanism is reattached.

The present invention also includes a pump mechanism that can either be used while connected to the holder or removed and used remotely. Under this variation, the pump mechanism is again connected to the holder in a way so that the chamber in which negative and positive pressure is created is in fluid communication with the air volume located between the flexible insert and the holder. The embodiment of this detachable handle can be a squeeze pump or any device that moves air to create pressure, such as a bellows, a piston or diaphragm. When the detachable pump is removed from the holder, a hose connects the pump to the holder to create pressure in the air volume.

The present invention also includes a breast pump assembly for pumping of a breast that has a funnel, a holder, a container and a pressure source. The funnel has a size and shape that allows for receiving of the breast. The holder has a handle and is connected to the funnel. The handle has a gripping surface on at least a portion thereof. The gripping surface is made from a material that facilitates gripping of the handle and breast pump assembly. The container is releasably connected to the holder and is in fluid communication with the holder and the funnel. The pressure source is in fluid communication with the funnel for supplying a vacuum to the funnel for pumping of the breast.

The pressure source can be an automatic pump or can be a manual pump. The gripping surface can have a plurality of gripping projections extending therefrom. The plurality of gripping projections can be equi-distantly spaced apart along the handle. The holder can have a second gripping surface that is on a diametrically opposite side of the holder from the handle, that is made from a material that facilitates gripping thereof. The automatic pump can be remotely positionable from the funnel. The handle may have a wave-like shape. The housing may have a third gripping surface that is on a base of the housing that is made from a material that facilitates gripping thereof. The assembly can also have a flexible insert that is sealingly engageable with the funnel to define a an air volume that is in fluid isolation from the breast, where the air volume is evacuated thereby causing a vacuum to be applied to the breast.

BRIEF DESCRIPTION OF THE DRAWINGS

Other and further objectives, advantages and features of the present invention will be understood by reference to the following:

FIGS. 18 through 22 are views of alternative embodiments for the breast pump assembly;

DESCRIPTION OF THE INVENTION

Figure 1:
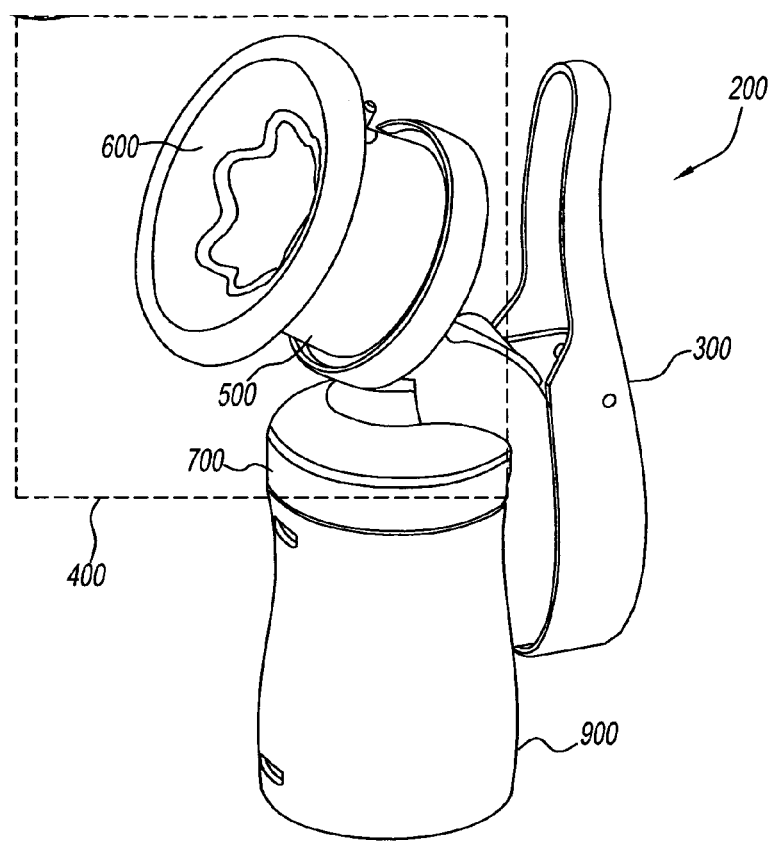
FIG. 1 is a perspective view of the Manual Breast Pump assembly.
Figure 2:
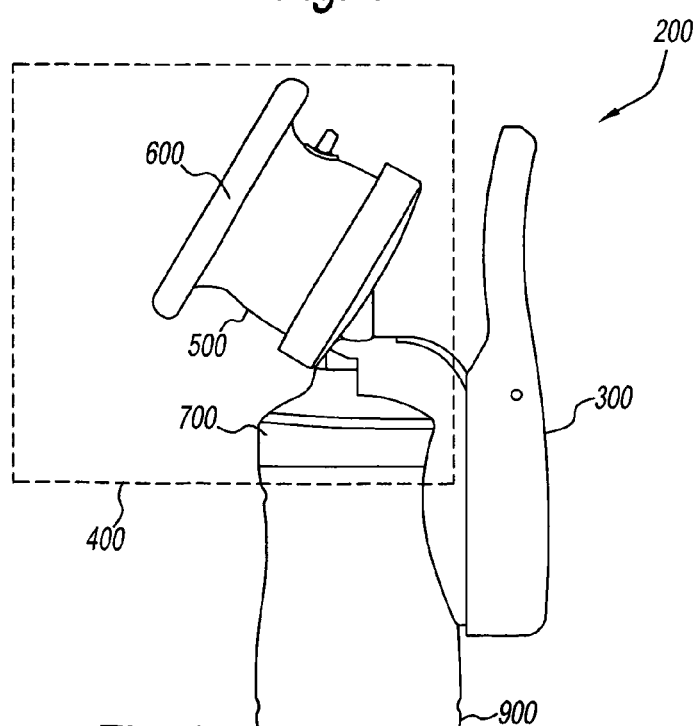
FIG. 2 is a side view of the assembly of FIG. 1.
Figure 3:
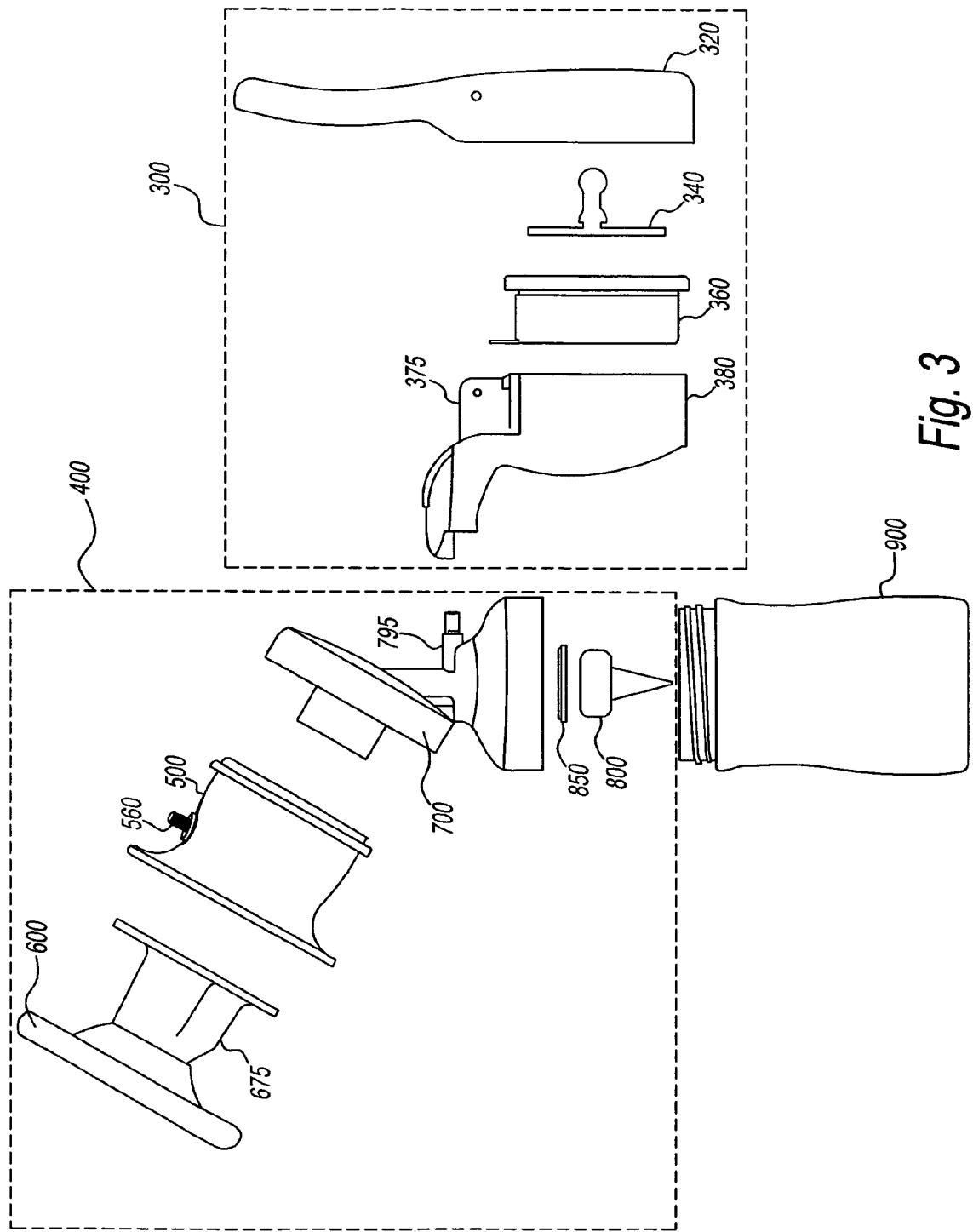
FIG. 3 is an exploded view of the assembly of FIG. 1.

Referring to the drawings and in particular FIGS. 1 through 3, there is shown a preferred embodiment of a breast pump generally referred to by reference number 200. The breast pump 200 has a pump mechanism 300, a breast cup 400 and container 900.

Breast cup 400 has a housing 500, a flexible insert 600, a holder 700 and a one way valve 800 (shown in FIG. 3).

Referring to FIG. 3, pump mechanism 300 has a handle 320, an actuator 340, a chamber diaphragm 360, and a holder attachment or diaphragm housing 380.

Referring to FIGS. 1 through 4, housing 500 is preferably a rigid or substantially rigid structure formed by a circumferential wall 505 defining a housing volume 510. Circumferential wall 505 preferably has a funnel shape with a generally hour-glass-shaped cross-section. Housing 500 has an outer section 520, a middle section 550 and an inner section 580. In this embodiment, outer section 520 generally has a diameter that is larger than the diameters of middle section 550 or inner section 580. Circumferential wall 505 of outer section 520 has a radius of curvature that is smaller than the radius of curvature of the circumferential wall at middle section 550 or inner section 580. Alternative shapes can also be used for breast cup 400 and housing 500. However, the shape of this embodiment provides for a wide or enlarged outer section 520 that facilitates engagement of breast cup 400 with a user's breast.

Outer section 520 has an outer end 525 that is adapted for engagement with insert 600. Outer end 525 preferably has a generally uniform cross-section and uses a tongue and groove connection to engage with insert 600. This type of engagement between outer end 525 and insert 600 allows a user to engage the outer end with the insert at any orientation or alignment to facilitate assembly. However, alternative securing structures can also be used, such as, for example, a projection or number of projections formed on outer end 525 that engage with corresponding grooves or orifices formed in insert 600.

Figure 4:
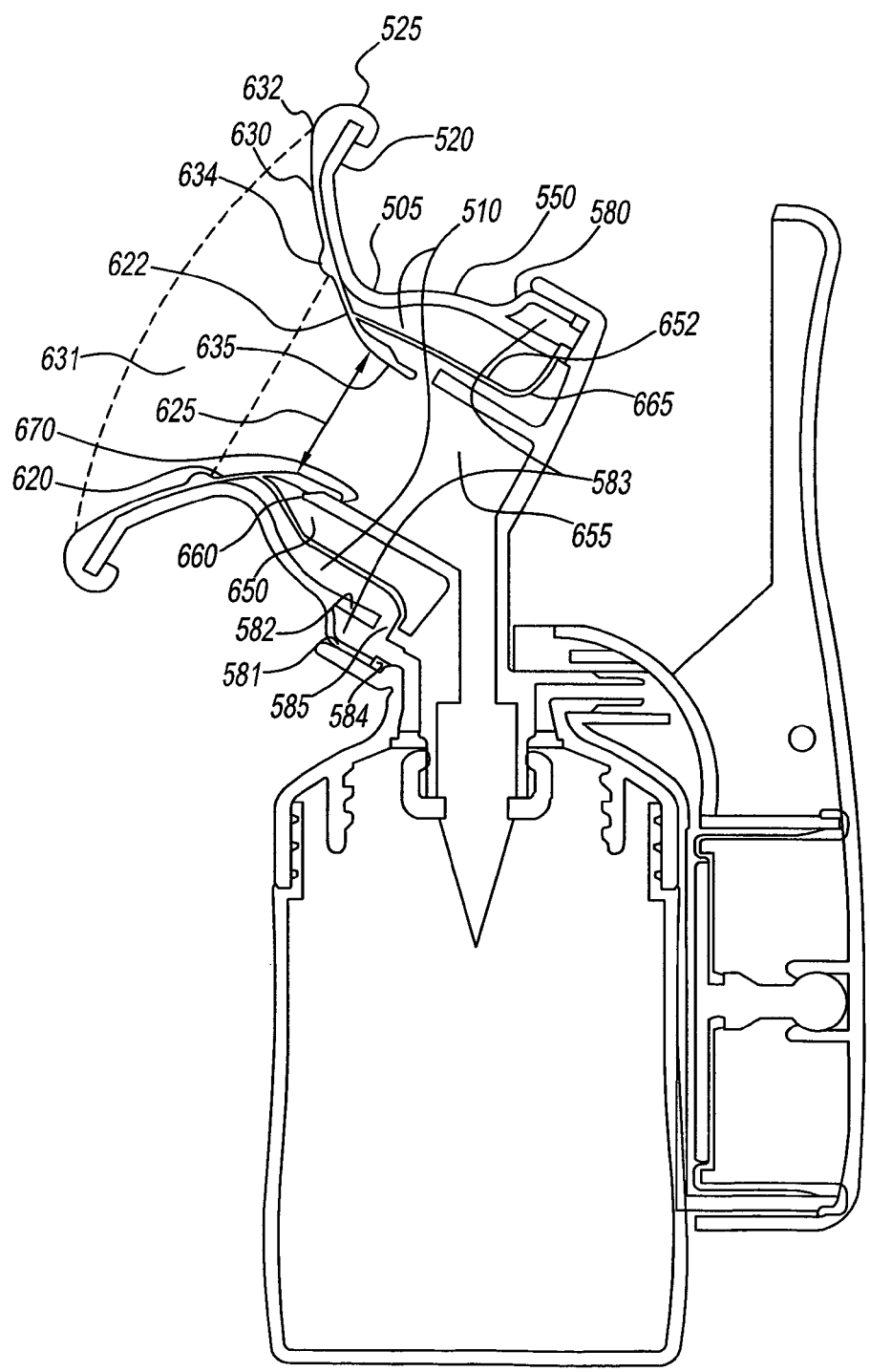
FIGS. 4 and 5 are cross-sectional views of the assembly of FIG. 1.

Although not shown in the view of FIG. 4, middle section 550 of housing 500 can have an air orifice 560 formed through circumferential wall 505, as shown in FIGS. 1 through 3. Air orifice 560 allows for alternative use of the breast pump 200 with a remote pump mechanism, whether manual or automated, as will be discussed later in greater detail. Air orifice 560 can also have a flow control mechanism (not shown) that allows the user to choose between the remote pump mechanism and the pump mechanism 300.

Preferably, air orifice 560 is a projection extending outwardly from circumferential wall 505 and has a central opening formed therethrough. The central opening provides for fluid communication through air orifice 560 into inner volume 510. Preferably, air orifice 560 has a cylindrical shape and is substantially perpendicular to circumferential wall 505. More preferably, air orifice 560 has a height and diameter that allows for a friction fit with air tubing or conduit (not shown). Air orifice 560 can also have a securing structure connected thereto (not shown), such as, for example, a retaining ring or have a shape, such as, for example, inwardly tapered, to facilitate securing of air tubing or conduit with the air orifice.

Inner section 580 of housing 500 has two retaining walls, outer wall 581 and inner wall 582, thereby forming annular chamber 583. Preferably, outer and inner walls 581 and 582 are concentrically aligned. Outer retaining wall 581 forms a seal with holder 700 through sealer or sealing member 584. The embodiment of FIG. 4 shows this sealer 584 as a continuous sealing ring, which allows the user to insert the housing 500 at any orientation to holder 700. However, other mechanisms in which the inner section 580, and specifically outer wall 581, are sealed to holder 700 may be used, such as, for example, corresponding tongue and groove seals on inner section 580, more precisely outer wall 581, and holder 700. Inner wall 582 has an opening 585 that allows annular chamber 583 to be in fluid communication with housing volume 510. This opening can be a single opening, or a series of openings along the circumference of inner wall 582.

Inner wall 582 of inner section 580 is also adapted for engagement with insert 600. With the exception of opening 585 or any other mechanism used to allow fluid communication between annular chamber 584 and housing volume 510, inner wall 582 preferably has a generally uniform cross-section and can use any mechanism for engaging with insert 600, such as a tongue and groove. This type of engagement between inner wall 582 and insert 600 allows a user to engage the inner end with the insert at any orientation or alignment to facilitate assembly. However, alternative securing structures can also be used, such as, for example, a projection or number of projections formed on inner wall 582 that engage with corresponding grooves or orifices formed in insert 600.

Insert 600 has a size and shape that allows for assembly of the insert to the housing 500 with sealing engagement of outer end 525 and inner wall 582 of the housing with the insert. Insert 600 has an outer portion 620 and an inner portion 650. Outer portion 620 has a substantially conical shape with a first side wall 622 defining an outer volume 625. Outer portion 620 has a first end 630 having an inner surface 631, and a second end 635. First sidewall 622 converges or tapers towards inner portion 650.

Inner portion 650 has a substantially cylindrical shape with a second side wall 652 defining an inner volume 655. Inner portion 650 has a third end 660 and a fourth end 665. Outer portion 620 is preferably integrally formed with inner portion 650 so that second end 635 of the outer portion is in inner volume 655 and a circumferential gap or space 670 is provided between the second end of the outer portion and third end 660 of the inner portion.

First end 630 of outer portion 620 has an outer fastener 632 and a massaging member 634. In this embodiment, outer fastener 632 is a groove in first end 630 with a size and shape that corresponds to outer end 525 of housing 500 for a tongue and groove connection between the housing and insert 600. Preferably, first end 630 of insert 600 is curled over to form the groove for the tongue and groove connection. This connection provides for sealing engagement between housing 500 and insert 600 at first end 630 of the insert and allows for connection of the housing and the insert at any orientation or alignment.

Massaging member 634 is a projection or other change in the shape of insert 600 in the area of outer portion 620, which makes contact with or is in proximity to the user's areola region. Massaging member 634 provides the user with a massaging action on the areola region, which facilitates expression of breast milk. In this embodiment, massaging member 634 is a continuous ridge having a star-like or wave-like shape. Preferably, massaging member 634 is integrally formed with insert 600 along inner surface 631 of first end 630.

Alternative shapes and sizes of massaging member 634 can also be used. Additionally, massaging member 634 can be a number of ridges, either continuous or portioned, and can also be concentrically or eccentrically aligned. The positioning of massaging member 634 along inner surface 631 depends on the size and shape of the massaging member that is used. Massaging member 630 is preferably disposed along inner surface 631 so that the massaging member traverses the areola region of the user's breast when breast cup 400 is in use. In the preferred embodiment, the star-like or wave-like shape of massaging member 634 provides more contact area between the massaging member and areola region as opposed to a circular shape.

Inner portion 650 has a number of folds or spacers 675 (as shown in FIG. 3) formed in second sidewall 652. Preferably, there are four spacers 675. spacers 675 have an upper end that are adjacent to or in proximity with circumferential wall 505 of inner section 580 of housing 500. Spacers 675 and second sidewall 652 form a number of bladders having bladder volumes. Preferably, there are four bladders. Spacers 675 are preferably substantially perpendicular to circumferential wall 505 of housing 500 and are barriers between the housing and insert 600 to provide additional structural integrity to inner portion 650 so that the bladder volumes do not fully collapse upon the housing.

As a result of the use of these bladders, it has been found that a lower level of suction is required for expressing breast milk. This is an improvement over conventional breast cups that do not have bladders because in such conventional breast cups some of the suction force is used in stretching the flexible insert material. An additional advantage of the use of the bladder design is that bladders prevent softer breasts from being sucked a substantial distance through outer and inner volumes 625, 655, which could impinge the pressurization of breast cup 400. Bladders provide a barrier for softer breasts against impingement. While this embodiment uses folds or pleats 675 in second side wall 652 as a barrier between the second side wall and housing 500, alternative barriers can also be used, such as, for example, projections or solid walls extending from the second side wall to the housing.

Although not specifically shown in this embodiment, the end of fourth end 665 can have a fastening mechanism to correspond to whatever mechanism is used on inner wall 582 to provide a seal between insert 600 and housing 500.

Insert 600 is made of a flexible material that is safe for contact with the breast milk. Such a flexible material is silicone. However, alternative flexible materials may also be used for flexible insert 600. When insert 600 is assembled to housing 500, the insert sealingly engages with the housing along outer end 525 and inner wall 582 of the housing so that volume 510, which is disposed between the insert and the housing, is in fluid communication with annular volume 583 and air orifice 560.

While the preferred embodiment in this invention is to use the pump mechanism 900 to apply the negative and positive pressures to the breast cup 400 through annular volume 583, the pressures can also be applied through the use of a breast pump connected to air orifice 560. A breast pump (not shown) can be placed in fluid communication with breast cup 400 via air tubing or conduit that is connected to air orifice 560. The breast pump can supply both a positive and negative pressure to breast cup 400. While this embodiment of breast cup 400 can apply both a positive pressure and a negative pressure to a user's breast, alternatively, only a negative pressure or only a positive pressure may also be applied to the user's breast with use of the breast cup. Additionally, either an automatic or a manual breast pump can be connected to breast cup 400 via the air tubing to supply a positive pressure, a negative pressure or both.

The expandable and contractible volume disposed between insert 600 and housing 500 provides an upper limit to the amount of negative pressure that can be applied to a user's breast. The sealing engagement of insert 600 and housing 500 provides a barrier between the user's breast and the vacuum source to prevent any breast milk from entering the air tubing, breast pump or the pump mechanism 300.

Figure 5:
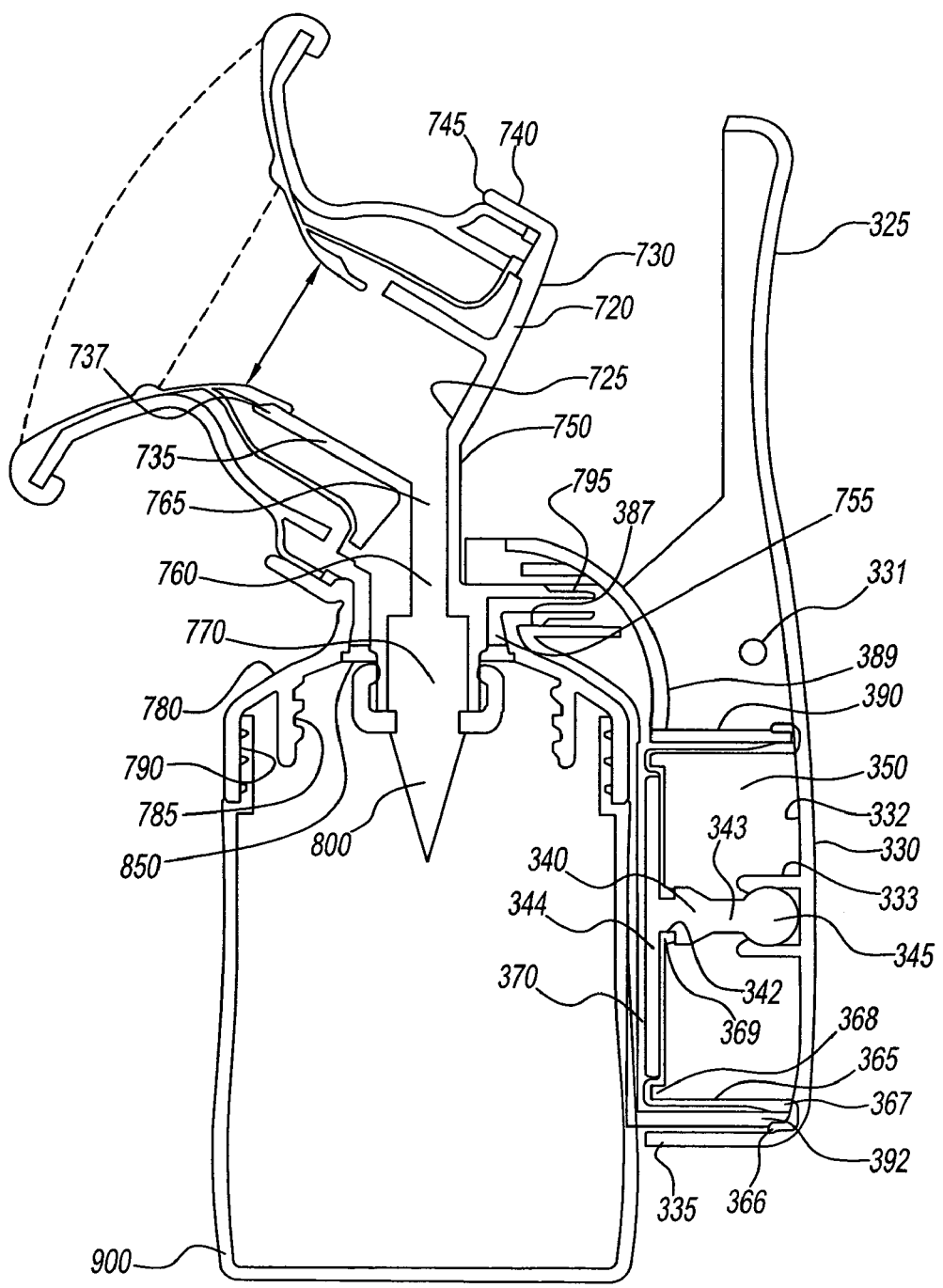
Figure 6:
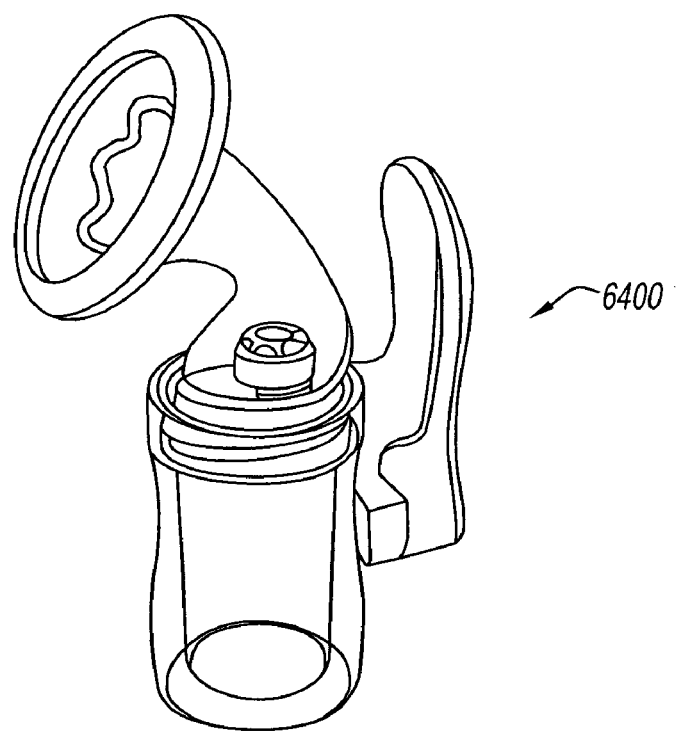
FIGS. 6 through 8 are an alternative embodiment of the Manual Breast Pump assembly.
Figure 7:
Figure 8:
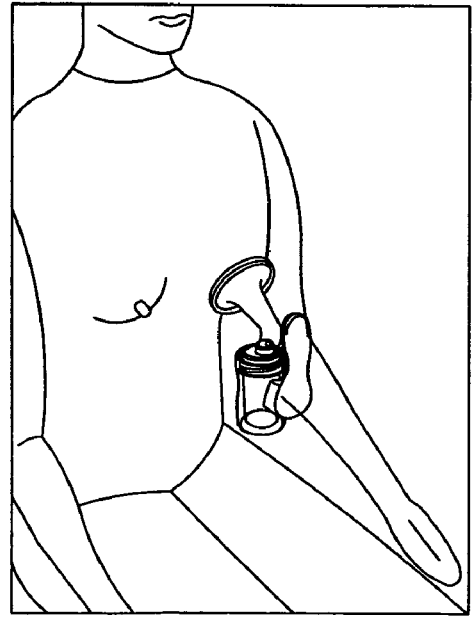

Referring to FIG. 5, holder 700 has a back plate 720, a support rod 750 and a base 780. Back plate 720 has a circular shape with an inner surface 725, an outer surface 730 and a flange 740.

Inner surface 725 of back plate 720 has a barrier member 735 extending therefrom. Barrier member 735 has a distal end 737. Preferably, barrier member 735 has a substantially cylindrical shape and is substantially perpendicular to back plate 720. When housing 500 and insert 600 are assembled to holder 700, distal end 737 of barrier member 735 is in circumferential space 670 between outer portion 620 and inner portion 650 of the insert. Barrier member 735 is substantially adjacent to the bladders and inner volume 655 of insert 600. Barrier member 735 is a rigid barrier between inner volume 655 and the bladders to prevent the breast from making contact with and impinging the bladders, which would reduce the amount of their inflation and deflation and thus reduce the reciprocating pressure applied to the breast. Barrier member 735 especially provides a rigid barrier for softer breasts against such impingement, which are more likely to extend beyond outer volume 625 of insert 600 into inner volume 655.

Referring to FIGS. 3, 4, and 5, flange 740 is a circular wall that surrounds inner surface 725 and extends towards housing 500. Flange 740 has a diameter larger than the diameter of inner section 580 of housing 500 so that the inner section, and more particularly outer wall 581, can be within the flange and substantially abut against inner surface 725. The diagrammed embodiment shows a fit between flange 740 and outer wall 581 that does not require any mechanical sealing mechanism. The diameters of outer wall 581 and holder 700 at flange 740 are close enough so that a secure and tight fit can be achieved merely by pressing them together. However, there may also be mechanical structures or methods for securing the housing 500 to the holder 700 that would be located at flange tip 745. One such example, and not limited thereto, can be a snap fit engagement that uses detents to secure the housing in place, with matching mechanisms for such fastening located on the housing. In one embodiment of a snap fit engagement, there would be three detents located throughout the flange 740 and the user would be able to secure the housing to the holder in any orientation or alignment.

Support rod 750 connects back plate 720 to base 780. Preferably, support rod 750 is secured to back plate 720 so that the back plate is angled slightly from the vertical, i.e., back plate 720 leans backwards. Support rod 750 has a supply channel 760 formed therein. Supply channel 760 has an upper end 765 and a lower end 770. Upper end 765 is connected to back plate 720 and is connected to tubular member 735. Lower end 770 is connected to base 780 and is in fluid communication with the base.

Base 780 has a concave disk-like shape with an inner securing member 785 and an outer securing member 790. Inner securing member 785 is a first set of threads and outer securing member 790 is a second set of threads. The dual thread arrangement of securing members 785 and 790 allows a user to connect base 780 to either standard reusable bottles or disposable liner holders which have differing diameters.

Valve 800 is a one-way valve that is sealingly engaged to lower end 770 of supply channel 760. One-way valve 800 allows the breast milk to flow into a container 900 that is secured to base 780 of holder 700, but prevents the negative pressure from sucking the milk out of the bottle. Preferably, valve 800 is a duckbill valve. However, alternative one-way valves can also be used.

In operation, the expansion and contraction of insert 600 as described above, causes breast milk to be expressed from the user's breast. The breast milk flows through inner volume 655 of inner portion 650 of insert 600 and through tubular member 735 of holder 700. The breast milk then flows through supply channel 760, through one-way valve 800, and into a container 900, which has been secured to base 780 of holder 700.

Referring to FIGS. 3, 4, and 5, pump mechanism 300 is generally located so as not to impede the user's view of the breast cup 400 while in use. Holder attachment 380 connects with holder 700 at holder inlet valve 795. Holder attachment 380 has an inner surface 385 with a shape that conforms to the shape of holder base 780. Holder attachment 380 connects with holder inlet valve 795 so that a seal is formed at junction 387 therebetween.

In the embodiment of FIGS. 1 through 5, holder 700 and holder attachment 380 are shaped so that a tight fit is formed at junction 387 without the aid of any fastening mechanism. However, any securing device, such as a tongue and groove or snap fit system, located on holder 700, holder inlet valve 795, holder attachment 380, inner surface 385 or any other position that facilitates the formation of the seal at junction 387, may be used. Also, while the preferred embodiment rigidly connects the holder attachment 387 and the holder 700, the present invention contemplates semi-rigid and flexible connections between the holder and holder attachment to facilitate assembly and the pumping process.

Holder attachment 380 defines an inner volume 383. By securing a seal at junction 387, inner volume 383 is in fluid communication with inner holder volume 755. Inner holder volume 755 is in fluid communication with annular volume 583 (shown in FIG. 4). Inner volume 383, inner holder volume 755, and annular volume 583, therefore, are all in fluid communication with each other and in fluid isolation from the fluid volume that passes from the user's breast through breast cup 400 and flexible insert 600.

Holder attachment 380 also has outer surface 389, which generally conforms to the shape of holder base 780. Holder attachment 380 has attachment extension 390, which can be circular, that can engage with handle 320, actuator 340 and chamber diaphragm 360. Attachment extension 390 engages with chamber diaphragm 360 at extension edge 392. Chamber diaphragm 360 has u-shaped edge 366 and thick wall 367. U-shaped edge 366 sealingly engages extension edge 392 to form a circular tongue and groove connection. The extra thickness of the chamber diaphragm 360 at thick wall 367 ensures that there will be a tight enough fit with extension edge 392 so that chamber diaphragm 360 remains secure even when the pressure from the pump mechanism 300 is activated. Although the preferred embodiment shows a fastening method using a circular tongue and groove connection and an extra wall thickness to ensure a very tight fit, other fastening structures, methods or mechanisms such as, for example, a friction fit, may be used.

Chamber diaphragm 360 also has a casing wall 365 that defines pump volume 350. Casing wall 365 extends toward container 900, and then bends to accommodate a tight fit with actuator 340. Casing wall 365 bends to form a u-shaped edge 368 that bends around edge 341 of flat end or disc portion 344 of actuator 340. The casing wall 365 then extends upward so that casing tongue 369 sealingly engages an actuator groove 342 formed circumferentially in main actuator shaft 343. Although the embodiment of FIGS. 1 through 4a shows a tongue and groove fastening system between the actuator 340 and the chamber diaphragm 360, any fastening mechanism can be used.

The seal between actuator 340, chamber diaphragm 360 and holder attachment 380 defines an internal casing volume 370. Internal casing volume 370 is in fluid communication with inner volume 383.

The negative and positive pressures exerted on the breast cup are controlled by the user through manipulation of handle 320. Handle 320 has a grip point 325, a lower section 330, and an end point 335. Grip 325 is preferably made of a soft co-molded material, though other materials may be used. Lower section 330 has an inner, convex surface 332 that along with casing wall 365 and actuator 340 defines pump volume 350. Handle 320 is connected to holder attachment 380 by pivot tab 375 (shown in FIG. 3), at pivot point 331. Any fastener can be used to connect handle 320 to pivot tab 375 at pivot point 331. The user exerts a pressure on handle 320 at or near grip point 325, pulling it toward the breast cup 400. The preferred amount of rotation of the handle about the pivot point 331 is between about 10 and about 30 degrees, which ensures maximum comfort to the user. Grip 325 is shown in the preferred embodiment as having a concave shape to facilitate the ease of gripping, but other shapes or surface textures can also be used.

Handle 320 is connected to actuator 340 by a handle securement attachment 333 that snap fits to actuator end 345. Handle securement attachment 333 extends substantially perpendicular to inner surface 332 of handle 320. Actuator end 345 is wider circumferentially than main actuator shaft 343 to ensure that the fit of end 345 into securement attachment 333 is secure. Actuator end 345 preferably has a spherical or rounded shape to allow for some pivoting of securement attachment 333 with respect to actuator main shaft 343 as the handle 320 pivots about pivot point 331 as will be described below in greater detail.

When the user exerts a pressure by pulling grip 325 of handle 320 toward the breast cup 400, lower end 330 exerts a pulling pressure on actuator 340 at end 345. The flat end 344 of actuator 340 moves in the direction away from container 900. A negative pressure is thereby exerted on internal casing volume 370 as a result of the movement of chamber diaphragm 360. Because volume 370 is in fluid communication with inner volume 383, and therefore inner holder volume 755, annular volume 583 and housing volume 510, the movement of actuator 340 and chamber diaphragm 360 in this manner exerts a negative pressure on flexible insert 600 and thereby causes the expression of breast milk. Sealing ring 850 ensures that there is no pressure loss in container 900 and that there is no fluid communication between the air in the container and the ambient air in the pump mechanism 300. Sealing ring 850 connects to holder base 780 at a point below inner holder volume 755.

After exerting the pulling force on grip 325, when the user releases the grip, a positive pressure can also be created when actuator 340 and chamber diaphragm 360, return to their unbiased position. The positive pressure can be provided to the breast cup 400 by way of the same change of volumes as described above. Handle 320 can also have a biasing member (not shown), as well as a controllable level of biasing force for the biasing member. This biasing member facilitates cyclical movement of the handle, and can further be used for providing both the positive and negative pressure at breast cup 400.

One of the advantages of manual breast pump 200 is the simplicity of assembly and cleaning. Breast cup 400 has only four components, i.e., housing 500, insert 600, holder 700 and valve 800. These components can be readily snap fit together. Also, these components can be secured to each other under any orientation or alignment. Thus, a user does not have to spend time obtaining the correct alignment of the components prior to assembly. Further, the breast milk and airflow are sealingly separated by insert 600. Thus, breast milk cannot enter the pump mechanism 300 or enter the air tubing (for the alternative pumping method described above).

Another advantage of manual breast pump 200 (and other alternate embodiments of the present invention that use the manual pump) is the design of handle 320 of pump mechanism 300, namely that the handle extends upwards from the pump. This ensures better comfort and ergonomics for the average female user, since the pinky finger of the user's hand does not have to travel as far as it does in currently available models.

Also, holder 700 separates very easily from container 900 through the use of a simple threaded system. Pump mechanism 300 can also be easily detached from holder 700 at holder inlet valve 795. This allows for the easy cleaning of all surfaces of the holder 700, and for the easy reattachment of pump mechanism 300. Thus, the entire pump 200 is designed for easy assembly, disassembly, reassembly, and cleaning.

Referring to FIGS. 6 through 22, several alternative embodiments of a manual breast pump are shown. In FIGS. 6 through 10, manual breast pump 1200, pump mechanism 1300, breast cup 1400 and container 1900 are shown. The user inserts flexible insert 1600 into a housing 1500 of the breast cup 1400. Flexible insert 1600 has upper end 1610 that engages the user's breast. The preferred embodiment shows the flexible material of insert 1600 to be silicone, though other flexible materials are contemplated by the present invention. Additionally, the preferred embodiment shows housing 1500 and container 1900 to be made of polycarbonate, but other rigid materials are contemplated by the present invention. Through the pump mechanism that will be described later, breast milk is expressed into flexible insert 1600 through upper insert volume 1615. Upper insert volume 1615 is in fluid communication with lower insert volume 1650. The expressed milk passes through volumes 1615 and 1650 into container 1900 through one-way valve 1800. Valve 1800 performs in the same manner as valve 800 of manual breast pump 200. The preferred embodiment shows one-way valve 1800 to be made of silicone, but other materials are contemplated by the present invention.

Outer fastener 1625 of flexible insert 1600 connects to outer end 1525 of housing 1500. Much like the embodiment of breast cup 400 shown in FIGS. 1 through 4a, outer end 1525 preferably has a generally uniform cross-section and uses a tongue and groove connection to engage with outer fastener 1625. This type of engagement between outer end 1525 and outer fastener 1625 allows a user to engage the outer end with the outer fastener at any orientation or alignment to facilitate assembly. However, alternative securing structures can also be used, such as, for example, a projection or number of projections formed on outer end 1525 that engage with corresponding grooves or orifices formed in outer fastener 1625 of insert 1600.

Flexible insert 1600 has lower end 1675 that sealingly engages with holder 1700. In the preferred embodiment, holder 1700 is made of polycarbonate, but other rigid materials are contemplated by the present invention. Lower end 1675 has outer edge 1680 and inner edge 1690, which connect to holder 1700 at inner fastener 1785. Outer edge 1680 and inner edge 1690 sealingly engage with holder 1700 on either side of inner fastener 1785. Although the embodiment shown has a simple friction fit, any sealing mechanism may be used, such a tongue and groove or snap fit.

Housing 1500 has lower end 1575 that also sealingly engages with holder 1700. Lower end 1575 has lower fastening end 1595. Lower fastening end 1595 sealingly engages with holder 1700 at holder fastening notch 1795. The type of engagement shown between lower fastening end 1595 and holder fastening notch 1795, which is a snap fit mechanism, allows a user to engage the fastening end with the fastening notch at any orientation or alignment to facilitate assembly. However, alternative structures, methods or means for securing the two may be used. Inner housing volume 1550 is thus formed between flexible insert 1600, housing 1500, and holder 1700. Inner housing volume is in fluid isolation from upper insert volume 1615 and lower insert volume 1650.

Housing 1500 also has grip 1576. The user places her thumb in or along grip 1576 while exerting pressure on pump mechanism 1300 as described below. This allows for easier and more comfortable use of the breast pump. All alternate embodiments of manual breast pump 200 have a similar feature to grip 1576 at the base of the holder that allows for a more conformable use of the breast pump.

Lower end 1575 also has outer edge 1580. Housing 1500 sealingly engages pump mechanism 1300 between outer edge 1580 and lower fasten end 1595. Although a friction fit is used in this embodiment, alternative connection structures or methods can also be used so that pump mechanism 1300 is sealingly engaged to housing 1500. The sealing engagement described above allows external housing volume 1560 to be formed. External housing volume 1560 is in fluid communication with inner housing volume 1550 through inner housing opening 1555. Thus, any fluid that passes through flexible insert 1600 is in fluid isolation from the air, or other pressure medium in pump mechanism 1300. Inner housing opening 1555 can be either a single hole or a series of holes throughout lower fasten end 1595.

Pump mechanism 1300 has internal chamber volume 1325, which is in fluid communication with external housing volume 1560. Internal chamber volume 1325 is defined in part by an internal chamber wall 1330, which is circumferentially surrounded by an external chamber 1335. An external chamber liner 1345 sealingly engages with internal chamber wall 1330 at junction 1340. The preferred embodiment shows the flexible material of external chamber liner 1345 to be silicone, though other flexible materials are contemplated by the present invention. Internal chamber volume 1325 and external chamber 1335 are thus in fluid isolation. The present invention has a tongue and groove connection between the chamber liner 1345 and the chamber wall 1330 at junction 1340, although other structures, methods or means are contemplated for securing the chamber liner to the chamber wall.

The chamber liner 1345 is made from a flexible material that retains a seal at junction 1340. Such a flexible material includes, but is not limited to, rubber or silicone. Preferably, the material is silicone.

External chamber liner 1345 has an outer end 1350. The pump mechanism 1300 has a handle 1375 and a lower end 1360. In the preferred embodiment, handle 1375 is made of ABS plastic, but other rigid materials are contemplated by the present invention. Outer end 1350 of chamber liner 1345 sealingly engages with lower end 1360 of pump handle 1375. The embodiment shown uses a tongue and groove connection, but other structures, methods or means of securing external chamber liner 1345 to pump handle 1375 may be used so that a seal is formed.

The pump handle 1375 has an upper end 1380. Although in this embodiment upper end 1380 has an upper concave shape transitioning into a lower convex shape in the direction away from housing 1500, other shapes of the handle may also be used.

The user exerts pressure on upper end 1380 by pulling it toward the breast cup 1400. This movement causes the lower end 1360 of the handle 1375 to move away from junction 1340, thereby producing a negative pressure in internal chamber volume 1325. Since external chamber liner 1345 is sealingly engaged to pump handle 1375, there is no pressure loss from internal chamber volume 1325. Further, because internal chamber volume 1325 is in fluid communication with external housing volume 1560, inner housing opening 1555, and inner housing volume 1550, a negative pressure is communicated to, and exerted on, flexible insert 1600, thereby exerting the negative pressure on the user's breast, and causing the expression of breast milk. Additionally, as will be described later in greater detail, the negative pressure is developed surrounding the areola region to facilitate expression of breast milk, as compared to contemporary breast pumps that create a negative pressure, and, thus, a negative force, downstream of the areola region resulting in an uncomfortable and inefficient longitudinal pulling force.

Figure 9:
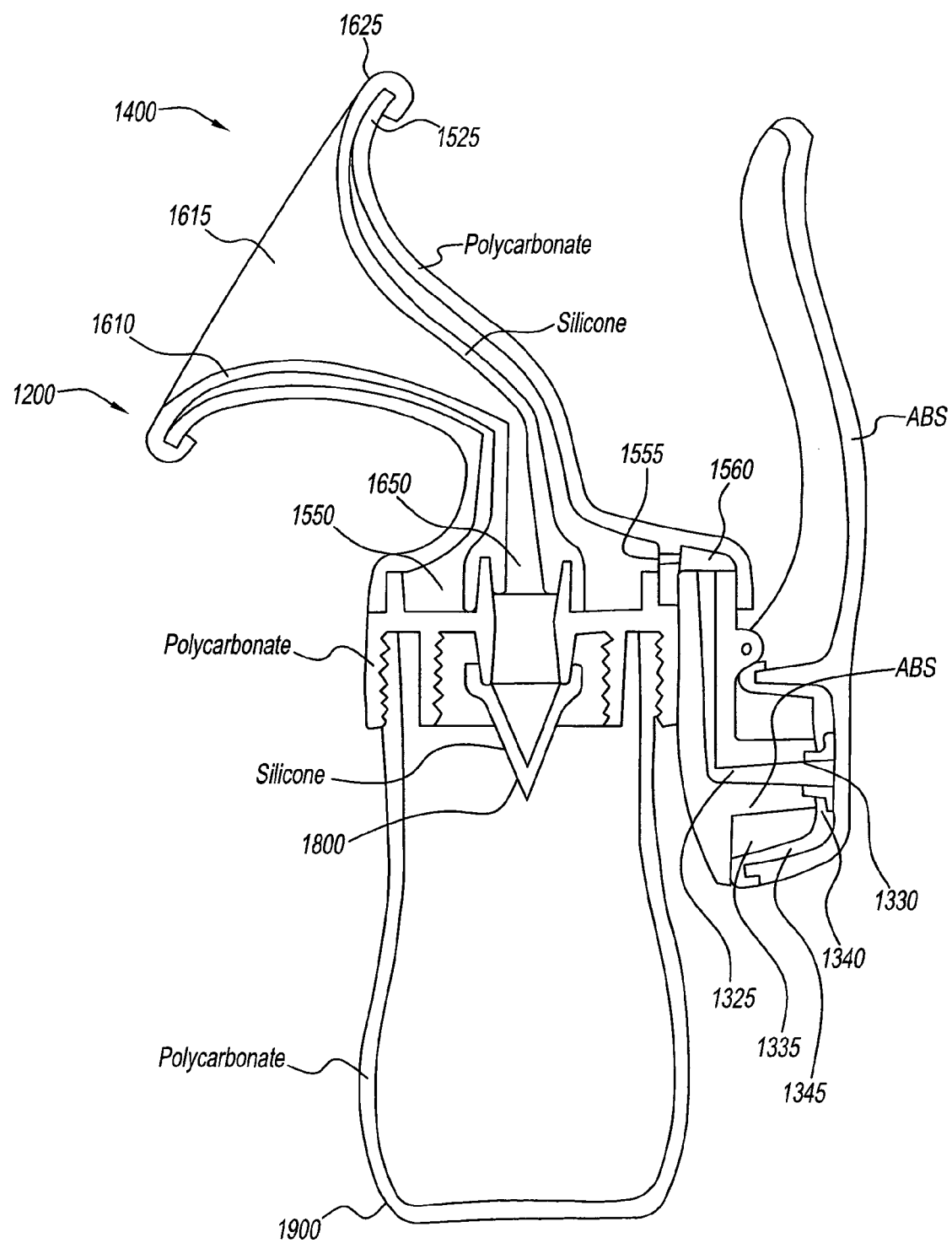
FIGS. 9 and 10 are exploded cross-sectional views of the assembly of FIG. 6.
Figure 10:
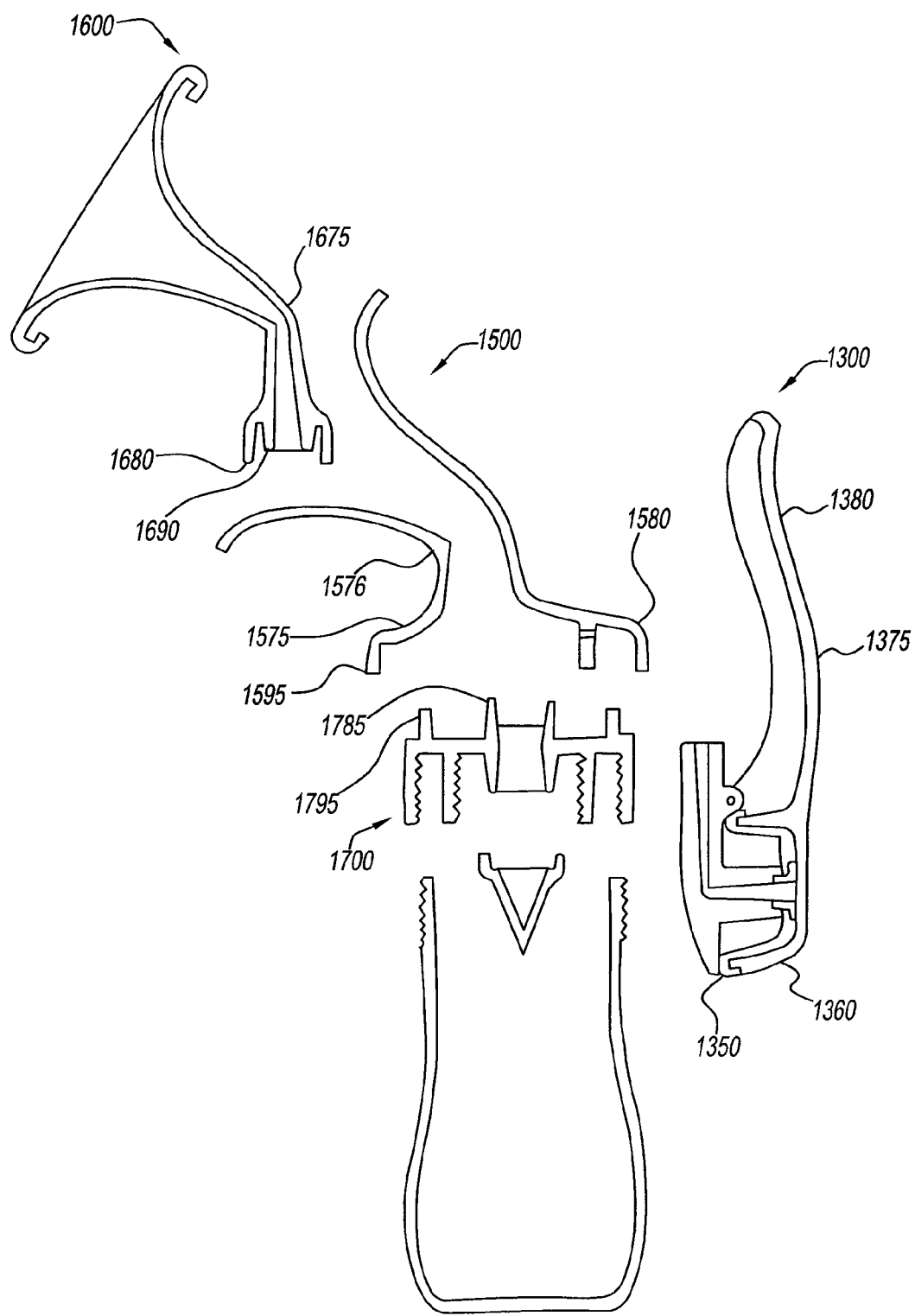

When the user releases pump handle 1375, a positive, massaging pressure can also be exerted on the breast through the return movement of air in the above-described volumes and openings. As shown in FIGS. 9 and 10, all of pump mechanism 1300 can be removed from manual breast pump 1200. Also, housing 1500, flexible insert 1600, holder 1700 and container 1900 can be removed from manual breast pump 1200. This allows for easy cleaning of all components. The mechanism for connecting container 1900 to holder 1700 is the same as that previously described for container 900 and holder 700, respectively, although the present invention contemplates other structures, methods or means for connection. Holder 1700 also has an inner securing member similar to inner securing member 785 of holder 700, as shown in FIG. 5.

Figure 11:
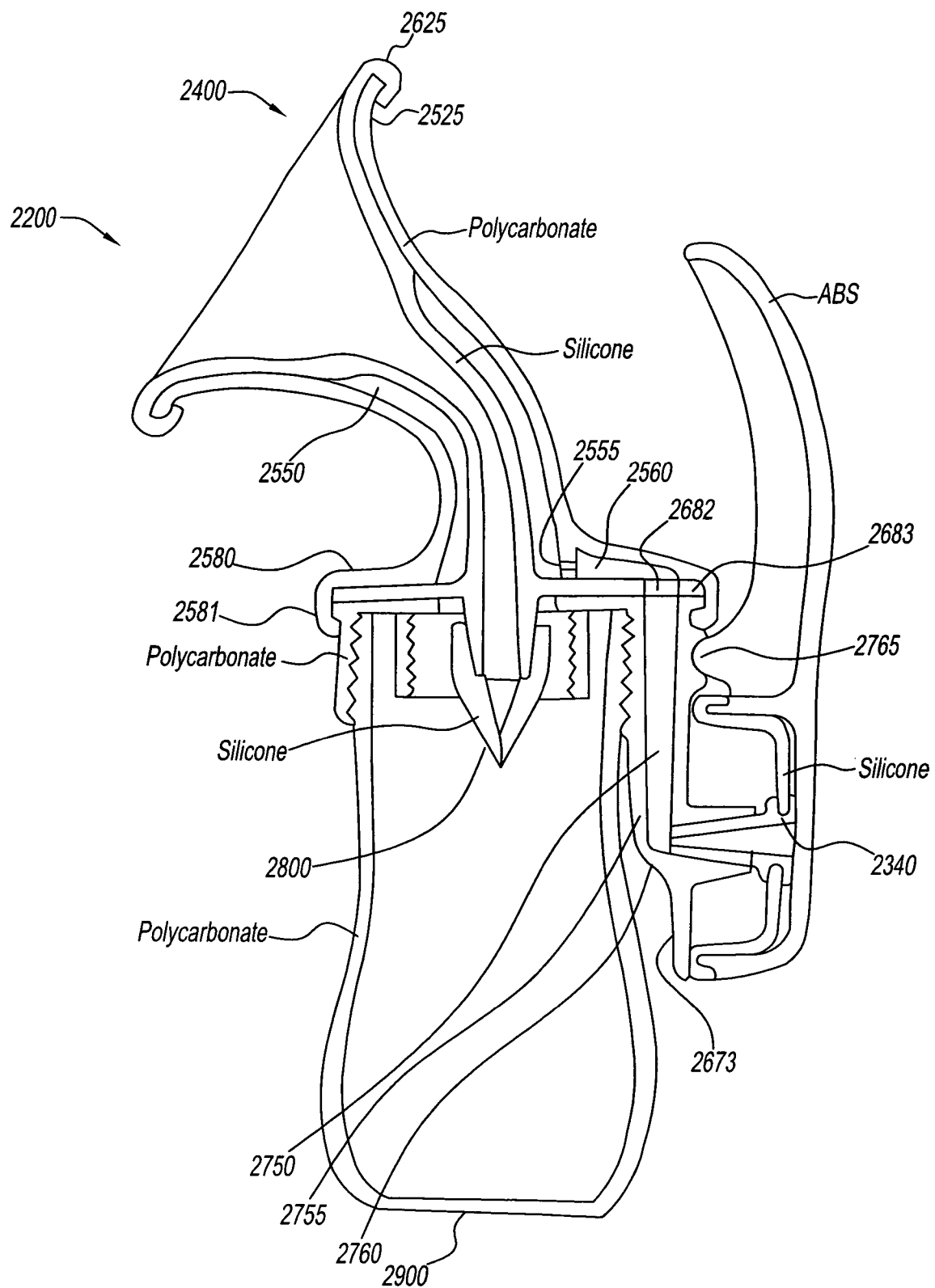
FIGS. 11 and 12 are exploded cross-sectional views of another alternative embodiment for the manual breast pump assembly.
Figure 12:
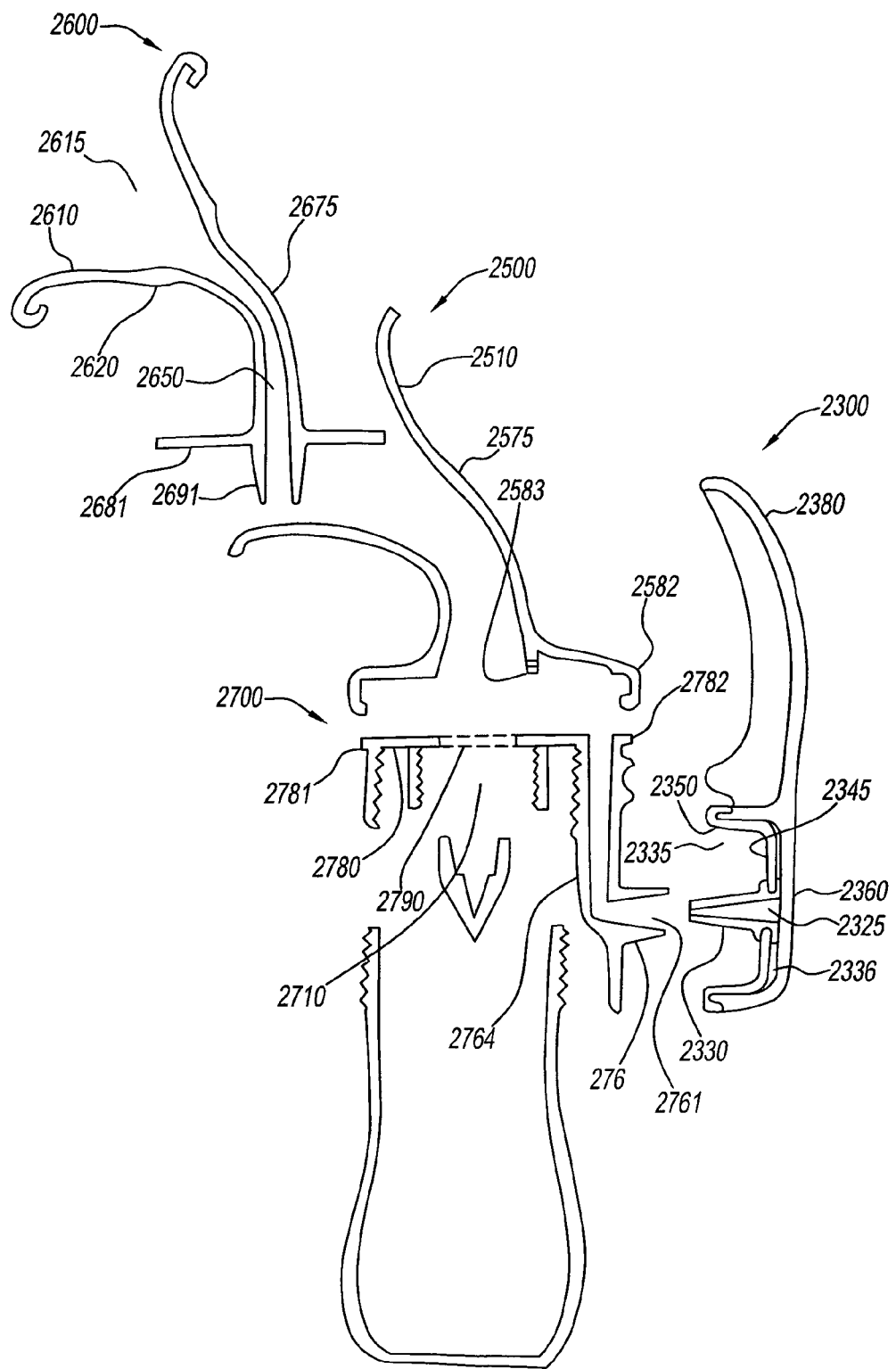

FIGS. 11 and 12 show another embodiment of a manual breast pump generally referred to by reference numeral 2200. Manual breast pump 2200 has a pump mechanism 2300, a housing 2500, a flexible insert 2600, a holder 2700, a one-way valve 2800 and a container 2900. The preferred embodiment shows the flexible material of insert 2600 to be silicone, though other flexible materials are contemplated by the present invention. Housing 2500, holder 2700, and container 2900 are made of a rigid material. Such a material includes, but is not limited to, polycarbonate. Preferably, the material is polycarbonate. One-way valve 2800 is made of a flexible material. Such a material includes, but is not limited to, silicone. Preferably, the material is silicone.

Flexible insert 2600 has an upper part 2610 and a lower part 2675. Upper part 2610 can engage the user's breast and has an upper insert volume 2615 through which the expressed breast milk flows. Upper part 2610 also has an outer fastener 2625, which functions in the same way as outer fastener 1625 of flexible insert 1600 in FIG. 6.

The upper part 2610 of flexible insert 2600 generally conforms to the shape of the upper part 2510 of housing 2500, thereby leaving little to virtually no air volume between them. Thus, when negative pressure is applied to flexible insert 2600 by pump mechanism 2300 as discussed below, the pressure that needs to be exerted is less than in other embodiments of the present invention and other conventional manual breast pumps. This consequently reduces the amount of pressure that has to be applied to the pump handle and the resulting amount of strain on the user's hand.

Flexible insert 2600 has an insert neck 2620 that is just below upper part 2610. Insert neck 2620 serves to reduce the diameter of the flexible insert from its larger value at upper insert volume 2615 to the lower value at lower insert volume 2650.

Upper part 2510 of housing 2500 further has outer end 2525. Outer end 2525 of housing 2500 sealingly engages outer fastener 2625 in the same way that outer end 1525 sealingly engages outer fastener 1625 in manual breast pump 1200, as discussed above. Lower part 2675 of flexible insert 2600 also has circular sealing member 2681 and circular extension 2691.

Housing 2500 has lower end 2575 that sealingly engages with holder 2700 and circular sealing member 2681. Lower end 2575 further has a lower housing 2580, a holder sealing edge 2581, and a pump sealing edge 2582. The user pulls flexible insert 2600 through the inside of housing 2500 such that circular sealing member 2681 aligns with the underside of lower housing 2580. Holder sealing edge 2581 then sealingly engages holder 2700 at edge 2781, so that sealing member 2681 is wedged between lower housing 2580 and holder face 2780. Although a snap fit is the preferred method of attachment shown, other structures, methods or means for fastening sealing edge 2581 to edge 2781 that produce a seal can be used. On the end of the pump where pump mechanism 2300 is attached, pump sealing edge 2582 sealingly engages holder 2700 at edge 2782, so that circular sealing member 2681 is also wedged between holder sealing edge 2582 and holder face 2780. Although the embodiment shown has a tongue and groove connection, other sealing structures, methods or means can be used. One embodiment of circular sealing member 2681 has member opening 2682 to engage in fluid communication with pump mechanism 2300 as described below. Other embodiments of sealing member 2681 may have a diameter that is short enough so that the sealing member extends to the edge of side chamber 2755 of holder 2700. A separate component 2683 could then be placed between pump sealing edge 2582 and edge 2782 to complete the sealing connection described above.

Housing 2500 has housing extension 2583 that extends from lower housing 2580, at the end of housing 2500 closest to the point at which pump mechanism 2300 is connected, toward holder face 2780. Housing extension 2583 has inner housing opening 2555, which can either be a single or a series of openings. When the sealing engagement between lower housing 2580, circular sealing member 2681, and holder face 2780 is formed as described above, housing extension 2583 extends to the surface of sealing member 2681 to form a seal. By completing this seal, external housing volume 2560 and inner housing volume 2550 are formed. Volumes 2550 and 2560 are in fluid communication with each other through inner housing opening 2555, and are in fluid isolation with any fluid that would pass through upper insert volume 2615 and lower insert volume 2650.

Also after completing this seal, circular extension 2691 of insert 2600 extends through holder opening 2790 into inner holder volume 2710. The diameter of holder opening 2790 is larger than that of circular extension 2691 to facilitate assembly by the user. By the process described above, however, when circular sealing member 2681 is sealed between housing 2500 and holder 2700, the air and liquid volume in container 2900 is kept in fluid isolation from external housing volume 2550. This ensures that none of the expressed breast milk is sucked up into the housing when negative pressure is applied to the housing volume by the pump mechanism 2300. After inserting flexible insert 2600 into inner holder volume 2710, the user connects one way valve 2800. One-way valve 2800 functions in the same manner as valve 1800 of manual breast pump 1200, with the exception that one way valve sealingly engages the flexible material of insert 2600 as opposed to the rigid structure of holder 1700.

Holder 2700 has a side end 2750, which pump mechanism 2300 connects to. Side end 2750 also has outer securing member 2764, which allows for connection of container 2900 to holder 2700. Side end 2750 also has side holder volume 2755, which is in fluid communication with external housing volume 2560 through circular member opening 2682. Side end 2750 extends downward along the edge of container 2900 and forms lower side end 2760 to interface with pump mechanism 2300. Lower side end 2760 has an interface volume 2761, an interface housing 2762, and an lower extension 2763.

Pump mechanism 2300 has a lower end 2360. Lower end 2360 has interface chamber 2330, internal interface volume 2325, external chamber 2335, and external chamber liner 2345. External chamber liner 2345 is made of a flexible material. Such a material includes, but is not limited to, silicone. Preferably, the material is silicone. External chamber liner 2345 sealingly engages interface chamber 2330 at junction 2340. Thus, interface 2325 and external chamber 2335 are in fluid isolation when the pump mechanism 2300 is connected to the holder 2700 as described below. This embodiment has a tongue and groove connection between sealing chamber liner 2345 and interface chamber 2330, but other structures, methods or means for securing the liner to the chamber may be used. Further, although this embodiment has the chamber liner 2345 made of silicone, alternative flexible, semi-flexible and partially flexible materials and/or combination of materials that retains a seal at 2340 may also be used.

External chamber liner 2345 also has an outer end 2350. Outer end 2350 of chamber liner 2345 sealingly engages with lower end 2360, forming internal pump volume 2336, which due to the seal is in fluid isolation with external chamber 2335. The embodiment shown is that of tongue and groove, but any mechanism or means to seal external chamber liner 2345 to lower end 2360 may be used.

Pump mechanism 2300 is connects to holder 2700. The user connects the pump mechanism 2300 to the holder 2700 by a snap-fitting connection at junction 2765. Other structures, methods or means for securing the pump mechanism 2300 to the holder 2700 that allow for easy assembly and removal by the user may also be used. The connection or fit between interface chamber 2330 and interface housing 2762 is such that a tight seal is formed between the two when the pump mechanism 2300 is attached to the holder 2700. The embodiment shown utilizes a friction fit. However, other structures, methods or means for securing the interface chamber 2330 and interface housing 2762 such that interface chamber remains secured to interface housing when negative pressure is applied to internal pump volume 2336 as described below, while still allowing for easy assembly by the user, may be used.

Pump mechanism 2300 has a handle 2380. Although in this embodiment the handle 2380 is in a convex shape in the direction away from the housing 2500, alternative shapes and/or dimensions can be used for the handle. Also, the preferred embodiment shows handle 2380 to be made of ABS plastic. However, handle 2380 may be made of other rigid materials. The user exerts pressure on handle 2380 by pulling it toward the breast cup 2400. The pump mechanism 2300 then pivots around junction 2765, which produces a negative pressure in internal pump volume 2336. Because external chamber liner 2345 is sealingly engaged to lower end 2360, no pressure is lost to ambient air. Further, because internal pump volume 2336 is in fluid communication with internal interface volume 2325, interface volume 2761, side holder volume 2755, and therefore inner housing volume 2550 through the channels described above, the pressure applied to handle 2380 exerts a negative pressure on flexible insert 2600 and the user's breast, to cause the expression of breast milk. When the user releases handle 2380, a positive, massaging pressure can be exerted on the breast through the same channels. As shown in FIGS. 11 and 12, all of the components of manual breast pump 2200 can be separately removed and cleaned, in much the same way as in manual breast pumps 200 and 1200.

Figure 13:
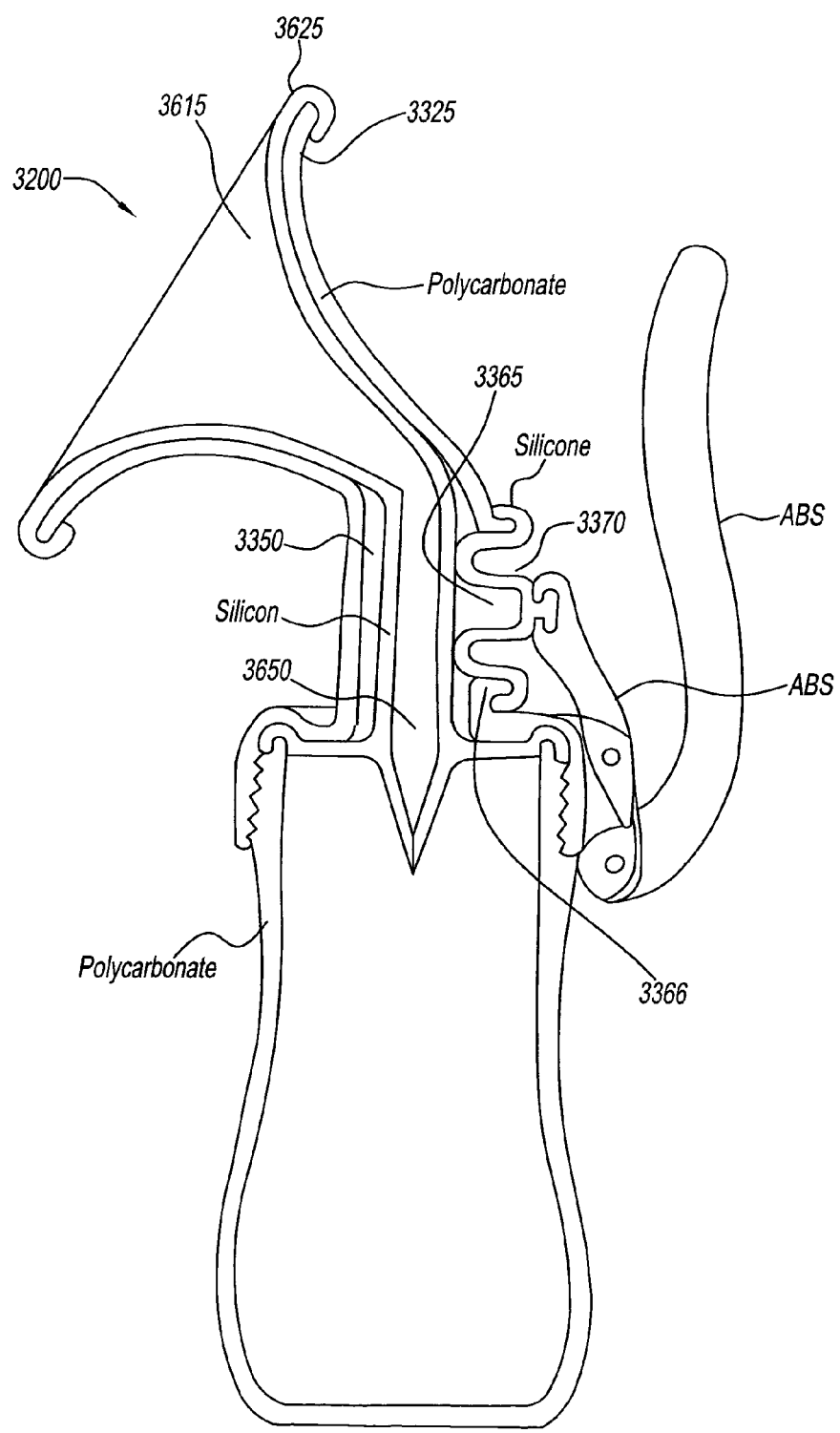
FIGS. 13 and 14 are exploded cross-sectional views of another alternative embodiment for the manual breast pump assembly.
Figure 14:
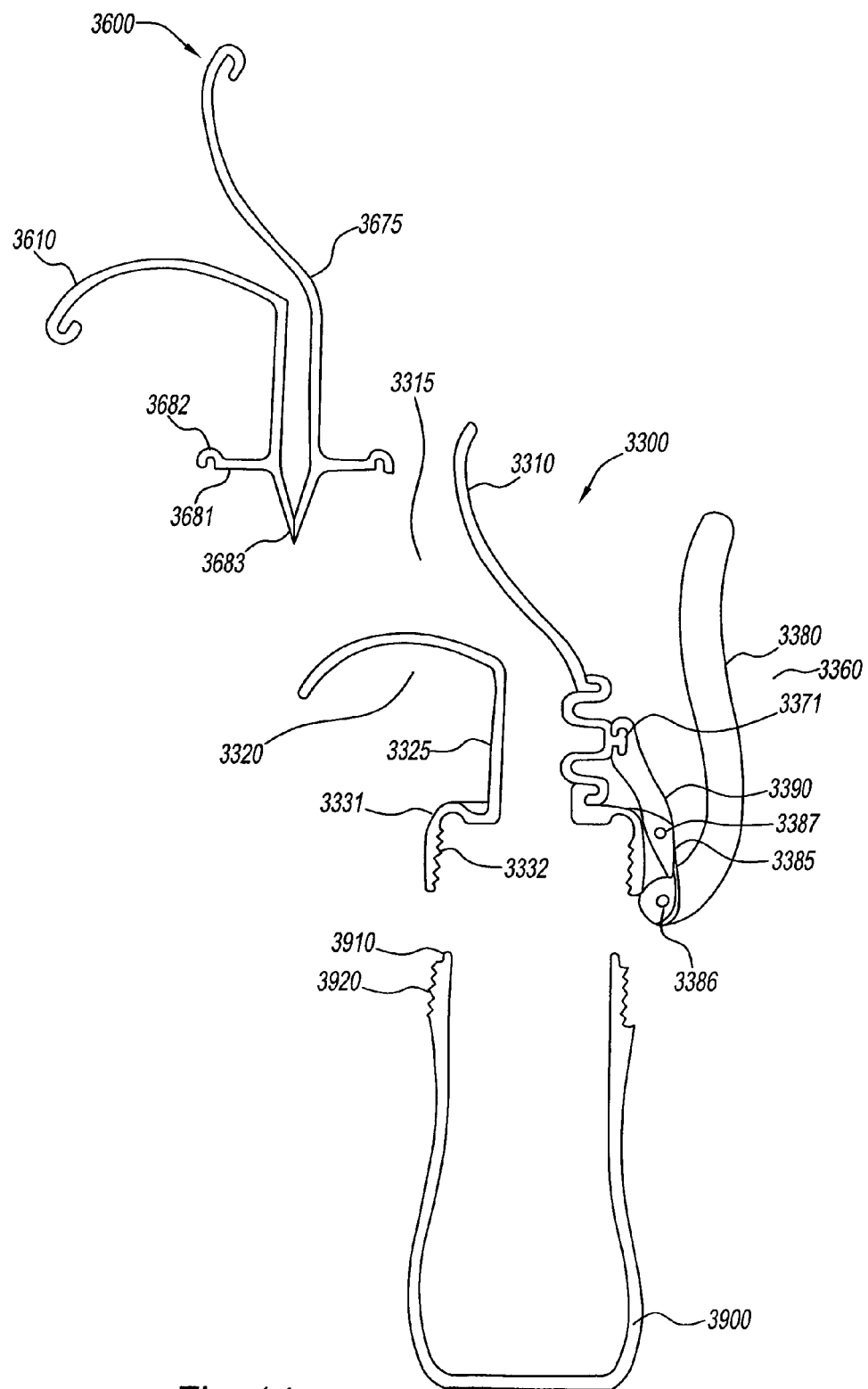

FIGS. 13 and 14 show another alternate embodiment of the manual breast pump generally referenced by numeral 3200. Manual breast pump 3200 has a pump system 3300, a flexible insert 3600 and a container 3900. Pump system 3300 combines the housing, holder, and pump mechanism of previous embodiments into one component. Also, the flexible insert 3600 combines the flexible insert and one way valves of previous embodiments into one component, as well. This allows for much easier assembly by the user.

Flexible insert 3600 is made of a flexible material. Such a material includes, but is not limited to silicone. Preferably, the material is silicone. The housing portion of pump system 3300 and container 3900 are made of a rigid material. Such a material includes, but is not limited to, polycarbonate. Preferably, the material is polycarbonate. The handle portion and pump levers of pump system 3300, discussed below, are also made of a rigid material. Such a material includes, but is not limited to, ABS plastic. Preferably, the material is ABS plastic.

Flexible insert 3600 has upper part 3610 and lower part 3675. Upper part 3610 engages the user's breast and has upper insert volume 3615 through which the expressed breast milk flows. Flexible insert 3600 is shaped so that upper part 3610 generally conforms to upper part 3310 of pump system 3300. The matching shape between upper part 3610 of flexible insert 3600 and upper part 3310 of pump system 3300 is such that there is little or virtually no air volume between them. Thus, when negative pressure is applied to flexible insert 3600 by pump mechanism 3300 as described below, the pressure that needs to be exerted is less than in other embodiments of the present invention and other conventional manual breast pumps. This consequently reduces the amount of pressure that has to be applied to the pump handle and the resulting amount of strain on the user's hand.

Flexible insert 3600 further has outer fastener 3625, and pump mechanism 3300 has outer end 3325. Outer fastener 3625 sealingly engages outer end 3325 in the same manner as the corresponding parts of manual breast pump 1200, as discussed above.

Lower part 3675 of flexible insert 3600 also has lower insert volume 3650, circular base 3681, outer sealing edge 3682, and dispensing valve 3683. When negative pressure is applied to the insert 3600 and consequently the user's breast as described below, the expressed milk flows through upper insert volume 3615, into lower insert volume 3650, and through dispensing valve 3683. Dispensing valve 3683 has a similar shape to the one-way valve of previous embodiments, namely that of a duckbill, and serves to keep the fluid in container 3900 from being sucked back up into flexible insert 3600.

Flexible insert 3600 directly, sealingly engages container 3900. In particular, outer sealing edge 3682 sealingly engages upper rim 3910 of container 3900. Although the shown embodiment illustrates a tongue and groove connection, other sealing structures, methods or means may be used, such as a snap fit or a simple friction fit.

Pump system 3300 has a pump housing 3320 and a pump 3360. Pump housing 3320 has a housing wall 3325 and a lower end 3330. Lower end 3330 sealingly engages with the flexible insert 3600 and the container 3900 so that the fluid and air volumes inside the insert and container are in fluid isolation from the air volume in the pump system 3300. In particular, lower end 3330 has a housing sealing groove 3331 that is formed in a curved shape so that outer sealing edge 3682 of flexible insert 3600 fits into the groove that is formed. Lower end 3330 also has sealing threads 3332 that correspond to sealing threads 3920 of container 3900. Thus, to assemble the pump, the user inserts flexible insert 3600 into upper opening 3315 of pump system 3300, and pulls it through so that outer sealing edge 3682 of the insert is aligned with the groove formed in housing sealing member 3331. The user then secures the insert to the upper part 3610 of the pump system 3300 as described above, and connects the components to the container 3900. By completing this seal, inner volume 3350 is formed, which is between housing wall 3325 and lower part 3330 of pump housing 3320, and in fluid isolation from the liquid volume that passes through upper insert volume 3615 and lower insert volume 3650.

On the side of pump housing 3320 where pump 3360 is connected, there is a housing orifice 3365 in housing wall 3325 that allows for the attachment of pump diaphragm 3370. Pump diaphragm 3370 sealingly engages pump housing 3320 at housing sealing edge 3366. This embodiment has a friction fit connection to complete this seal, but other sealing structures, methods or means, such as a tongue and groove or a snap fit seal, may also be used.

Pump 3360 has a pump handle 3380, a minor lever 3385, pivot points 3386 and 3387, and a major lever 3390. Although the diagram shows a concave upper part of the handle 3380 transitioning into a convex lower part in the direction away from the housing 3320, the present invention contemplates other shapes of handle 3380 that provide an easy grip for the user. Major lever 3390 is connected to diaphragm 3370 at diaphragm end 3371. The shown connection method of this embodiment is that of a tongue and groove, but other connection structures, methods or means to secure major lever 3390 to diaphragm 3370 may also be used.

The user applies pressure to pump handle 3370 by pulling it toward pump housing 3320. The pump handle then pivots around pivot point 3376, which applies a pressure to minor lever 3375. Minor lever 3375 then pivots around pivot point 3377, and exerts a pressure on major lever 3380 that pulls diaphragm 3370 away from pump housing 3320. This produces a negative pressure in inner volume 3350, and consequently a negative pressure on flexible insert 3600 and the user's breast. When the pump handle is released, a positive, massaging pressure can be applied to the breast through the same channels.

Figure 15:
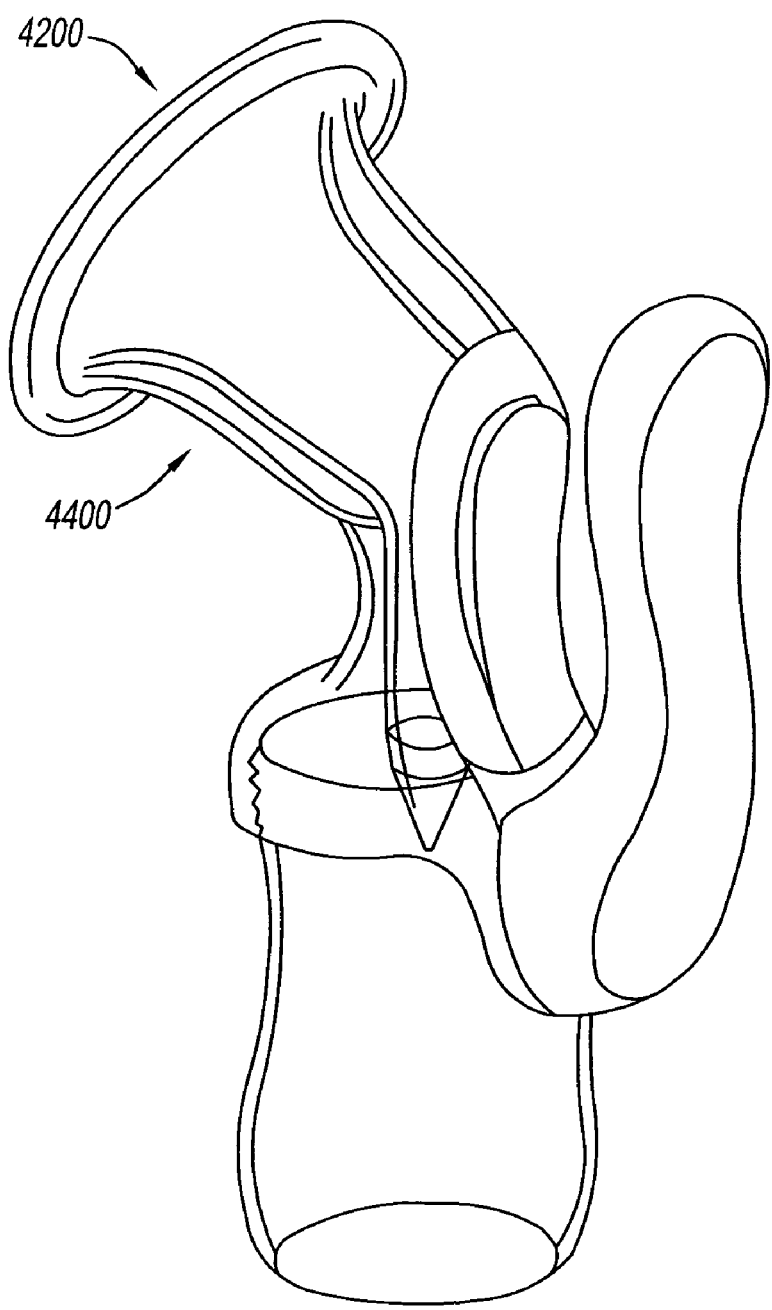
FIGS. 15 through 17 are views of an alternative embodiment for the breast pump assembly.
Figures 16, 17:
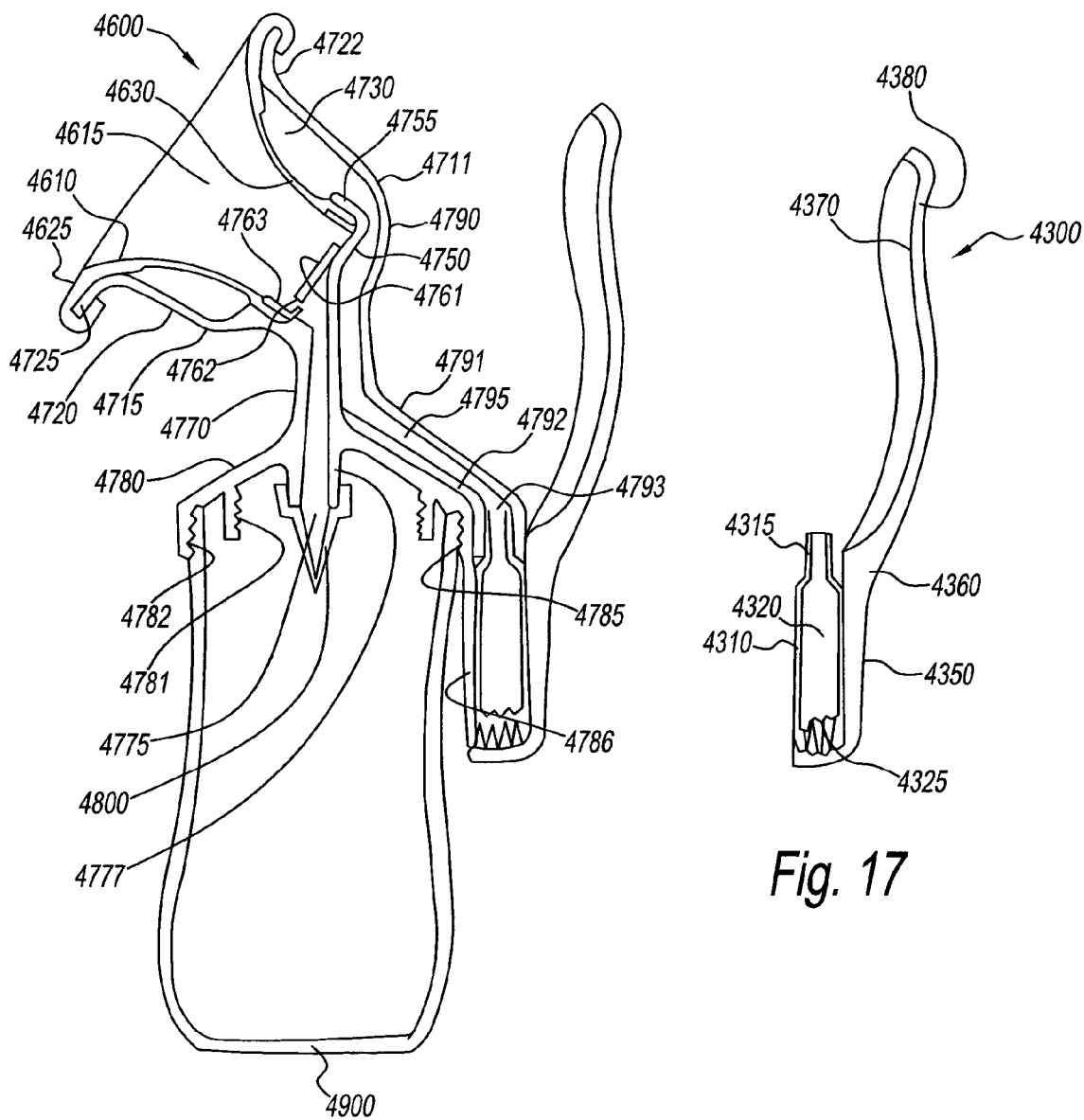
Figure 26:
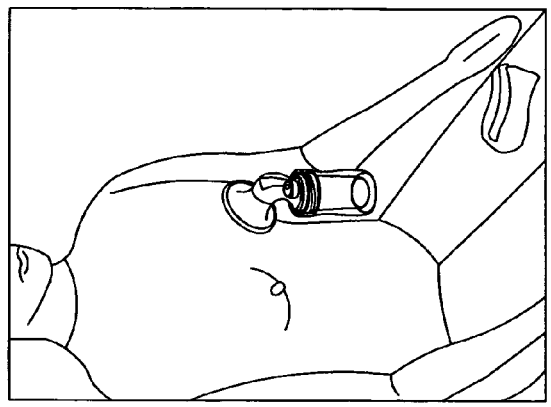
FIGS. 23 through 26 are views of an alternative embodiment of the breast pump assembly having a selectively detachable squeeze pump mechanism.
Figure 24:
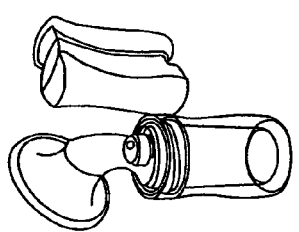
Figure 25:
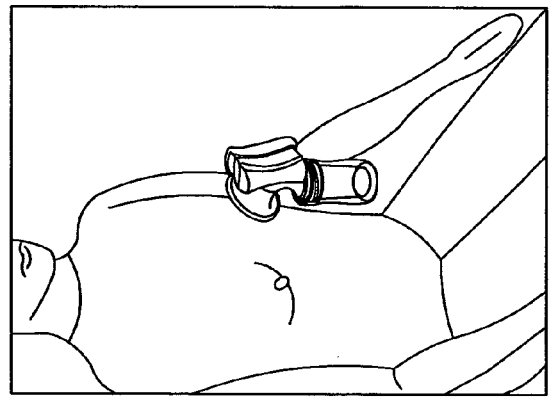
Figure 23:
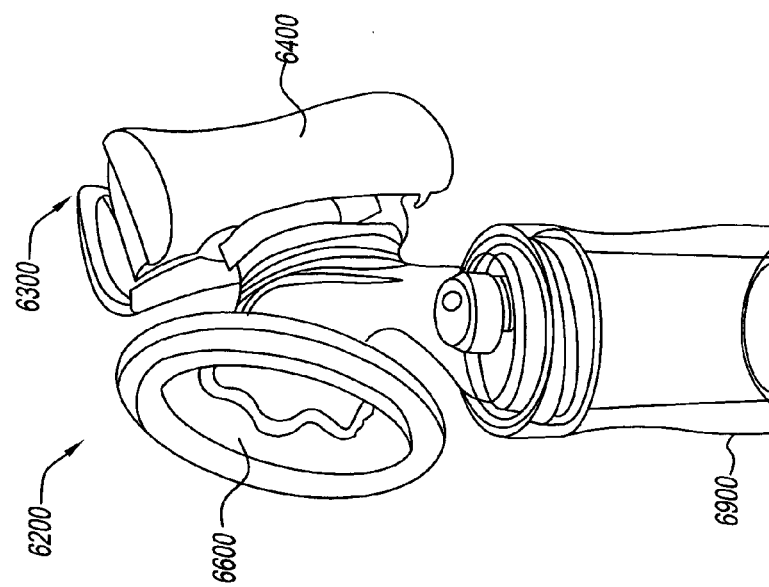

FIGS. 15 through 17 show another embodiment of the manual breast pump generally represented by reference numeral 4200, which has a detachable pump 4300, a breast cup 4400 and a container 4900. Breast cup 4400 also has a flexible insert 4600 and a holder 4700.

Flexible insert 4600 has upper part 4610, upper insert volume 4615, and outer fastener 4625. These parts function in substantially the same manner as their counterparts in previously discussed embodiments. Flexible insert 4600 also has lower part 4630 that has a smaller thickness than upper part 4610. In this embodiment of manual breast pump 4200, the user connects the flexible insert 4600 to holder 4700 by press-fitting lower part 4630 into the holder as described below.

Holder 4700 has housing 4710, back plate 4740, support rod 4770, base 4780, and pump attachment 4790. Housing 4710 has upper part 4720 and lower part 4715. Upper part 4720 has outer end 4725 that sealingly engages outer fastener 4625 of insert 4600 in the same manner as the corresponding components of previous breast pump embodiments.

Upper 4610 of insert 4600 and upper part 4720 of housing 4710 are shaped so that they generally conform to each other. When they are connected as described above, there is virtually no air volume between them. At bend 4722 of upper part 4720, the insert and housing begin to separate so that housing volume 4730 is formed.

Back plate 4740 has inner surface 4745, outer surface 4750, and back plate flange 4755. Inner dispenser 4760 is fastened to inner surface 4745. Inner dispenser 4760 has dispenser base 4761, dispenser orifice 4762, and dispenser flange 4763. Dispenser orifice 4762 can either be a single opening or multiple openings as shown. When the user assembles the pump, they press fit lower part 4630 of flexible insert 4600 between dispenser flange 4763 and back plate flange 4755. The spacing between dispenser flange 4763 and back plate flange 4755 is such that when lower part 4630 is fit between them, an airtight seal is formed. Thus, housing volume 4730 is in fluid isolation from the air and liquid volumes that pass through flexible insert 4600.

Support rod 4770 has inner volume 4775, which is in fluid communication with upper insert volume 4615 through dispenser orifice 4762. Support rod 4770 also has lower end 4777, which extends past base 4780 and sealingly engages one way valve 4800. One-way valve 4800 performs in the same manner as one-way valve 800 of breast pump 200, as described above. Thus, when negative pressure is applied to flexible insert 4600 as described below, the expressed milk flows through upper insert volume 4615, through dispenser orifice 4762, into inner volume 4775, and through one way valve 4800 into container 4900, all of which is in fluid isolation from housing volume 4730 and the pump mechanism 4300.

Base 4780 of holder 4700 has a concave disk-like shape with an inner securing member 4781 and an outer securing member 4782. These perform the same functions, respectively, as inner securing member 785 and outer securing member 790 of base 780 of breast pump 200. Namely, the dual thread arrangement allows a user to connect base 4780 to either reusable bottles or disposable liner holders that have different diameters.

Base 4780 also has a pump extension 4786 that extends from outer edge 4785 at the point of base 4780 where detachable pump 4300 is connected. Pump extension 4786 provides rigid support for the bladder mechanism used in detachable pump 4300.

Pump attachment 4790 is fastened to lower part 4715 of housing 4710 at housing end 4711. This can be a permanent fastening, or one that allows the user to removably detach the attachment as well. Outer wall 4791 of attachment 4790 extends down the side of breast cup 4400, and has a shape that generally conforms to back plate 4740, support rod 4770, and base 4780. Pump attachment 4790 also has inner wall 4792 that extends from the base of support rod 4770 along the surface of base 4880 to attachment opening 4793 where detachable pump 4300 is connected. Inner wall 4791 and outer wall 4792 are separated so that inner attachment volume 4795 is created. Inner attachment volume 4795 is in fluid communication with housing volume 4730.

Detachable pump 4300 has a pouch or flexible member 4310, a lower end 4350, and a handle 4370. Pouch 4310 can be a bladder or other bellows-type device that has a flexible wall that can be expanded to create a negative pressure at the opening. Pouch 4310 has neck 4315, internal pouch volume 4320, and lower pouch end 4325. Neck 4315 is of reduced diameter as compared to the rest of pouch 4310, and sealingly engages inner wall 4791 and outer wall 4792 of pump attachment at attachment opening 4793, so that internal pouch volume 4320 is in fluid communication with inner attachment volume 4795. The sealing connection in this embodiment is a friction or pressure fit, but alternative structures, methods or means to create the connection or seal may be used.

The user exerts a pressure on grip 4380 of handle 4370, which then pivots about point 4360. Grip 4380 can be made of a soft or resilient material, such as, for example, TPE, soft plastic or any other material that allows for easy manipulation of handle 4370. Lower end 4350 moves in a direction away from container 4900 when the handle 4370 is actuated, and causes pouch 4310 and internal pouch volume 4320 to expand. Internal pouch volume 4320 is in fluid communication with inner attachment volume 4795 and housing volume 4730. Therefore, the user generates a negative pressure by exerting pressure on handle 4370 that is communicated to, and exerted on, the flexible insert 4600, causing the expression of breast milk. When the user releases the handle, a positive, massaging pressure can be exerted on the breast through the same channels.

FIGS. 18 through 22 show another embodiment of the manual breast pump generally referenced by reference numeral 5200. Manual breast Pump 5200 functions in substantially the same manner as manual breast pump 200, with the exceptions noted below.

In manual breast pump 5200, the housing and holder are combined into one part, which is holder 5700. Manual breast pump 5200 also has a flexible insert 5600. Holder 5700 has a back plate 5720. Back plate 5720 has an inner surface 5725, a receptacle 5726, which is cut into the inner surface, a securing notch 5727, and a fastening hole 5728. Flexible insert 5600 has an upper end 5610, a lower end 5650, an insert sealing cap 5655, and a sealing end 5660. To assemble manual breast pump 5200, the user pulls flexible insert 5600 through the upper opening of housing 5700, and pulls sealing end 5660 through fastening hole 5728 so that the insert sealingly engages with housing 5700 at receptacle 5726. When the insert 5600 is pulled through the holder 5700 in this manner, sealing groove 5656 of sealing cap 5655 sealingly engages securing notch 5727. By completing this seal, inner housing volume 5710 is defined, and is in fluid isolation from any fluid and air volume that passes through flexible insert 5600. Thus, the expressed milk flows from the user's breast into upper insert volume 5615, through dispensing orifice 5657 of the flexible insert 5600, through holder orifice 5729, and into supply channel 5760.

The pump mechanisms 5300A and 5300B shown in FIGS. 20 and 22 operate in virtually the same manner as pump mechanism 300 of manual breast pump 200. In the embodiment shown in FIGS. 18 and 19, the pump mechanism 5300A differs from the pump mechanism 300 of FIGS. 1 through 5 in that the pump housing 5380 is integrally connected to the holder 5700 at holder inlet 5795. Further, outer edge 5781 of holder base 5780 extends along and down the side of the container 5900 to connect or fasten to the lower end 5382 of the pump housing 5380. In the embodiment shown in FIGS. 21 and 22, the size of the diaphragm of pump mechanism 5300B relative to the size of the internal pump chamber and the mechanism used to secure the diaphragm to the pump wall are different from the embodiment of manual pump 300.

FIGS. 23 through 26 show another embodiment of the manual breast pump generally referred to as reference numeral 6200. Manual breast pump 6200 has a pump mechanism 6300 that can be connected directly to the breast pump or can be detached from the breast pump. Manual breast pump 6200 functions in a substantially similar manner as the previous embodiments described above. Manual breast pump 6200 has a flexible insert 6600 that engages the user's breast, an insert volume that provides for flow through the insert into the container 6900 and is in fluid isolation from the air in the pump system 6300, and the pump mechanism 6300 that exerts a negative pressure on the insert and causes the expression of milk from the user's breast.

The pump mechanism 6300 can either be used while attached to the manual breast pump 6200, or removed and used remotely. When used remotely, the pump mechanism 6300 is connected to the housing of the manual breast pump 6200 by tubing or a hose (not shown). Such tubing can be biased for easy retraction into a storage position after being used. This allows the user to use the detachable pump mechanism 6300 in whichever configuration that is more comfortable. Also, using detachable pump mechanism 6300 in its remote configuration provides a smaller profile of manual breast pump 6200. This allows the user more flexibility in the use of the pump, for example under-the-shirt use. The pump mechanism 6300 has a pair of handles 6400 that are adapted to facilitate use and manipulation.

The pair of handles 6400 is smaller than contemporary handles found on breast pumps and are also more compact. The handles 6400 are movable with respect to each other to generate a pressure. To generate pressure, the present invention contemplates the use of, for example, a bellows, a diaphragm, a piston, or any other mechanism capable of producing a pressure in the pump mechanism 6300. The pressure can be applied in the positive direction, the negative direction, or both.

Additionally, handles 6400 provide for a squeezing motion that is in the direction between the user's fingers and palm, which provides a direction of pumping that can be easier for a user to manipulate.

Figure 27:
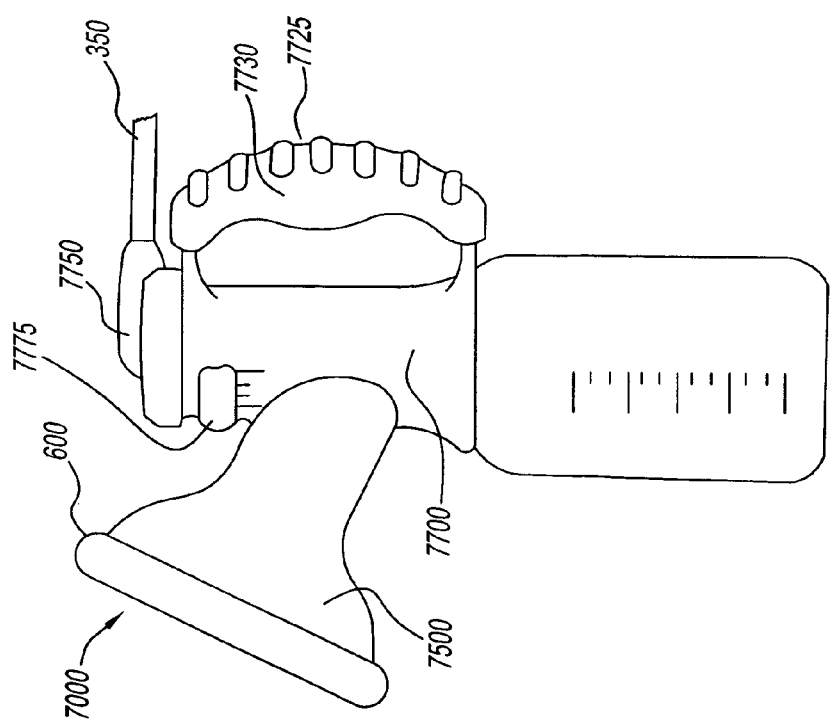
FIG. 27 is a plan view of another alternative embodiment of a breast cup of the present invention having gripping material on the handle.

Referring to FIG. 27, an alternative embodiment of the breast cup of the present invention is shown and generally represented by reference numeral 7000. Breast cup 7000 is shown as an automatic pump but is usable with a manual pump, including a pumping mechanism that is affixed thereto such as the previously described embodiments. Breast cup 7000 is usable with insert 600. Breast cup 7000 has a funnel shaped housing 7500 that is connected to a cylindrically-shaped holder 7700. Holder 7700 has a handle 7725, a pressure orifice 7750, and a pressure adjuster 7775. Handle 7725 is ergonomically contoured and has a wave-like shape 7730 that provides for different holding angles. Handle 7725 is disposed along holder 7700 on the opposing side from funnel 7500. Handle 7725 is preferably made of, or covered by, a material that facilitates gripping. Handle 7725 can include various textures, projections and/or embossments to sooth the user's hand during the pumping process.

Pressure orifice 7750 can be attached to tubing 350 to place breast cup 7000 in fluid communication with an automatic breast pump. Pressure adjuster 7775 is in fluid communication with pressure orifice 7750 and allows a user to adjust the pressure at the breast cup 7000 without having to make an adjustment at the breast pump. In this embodiment, pressure adjuster 7775 is a dial but alternative actuators can also be used.

Figure 28:
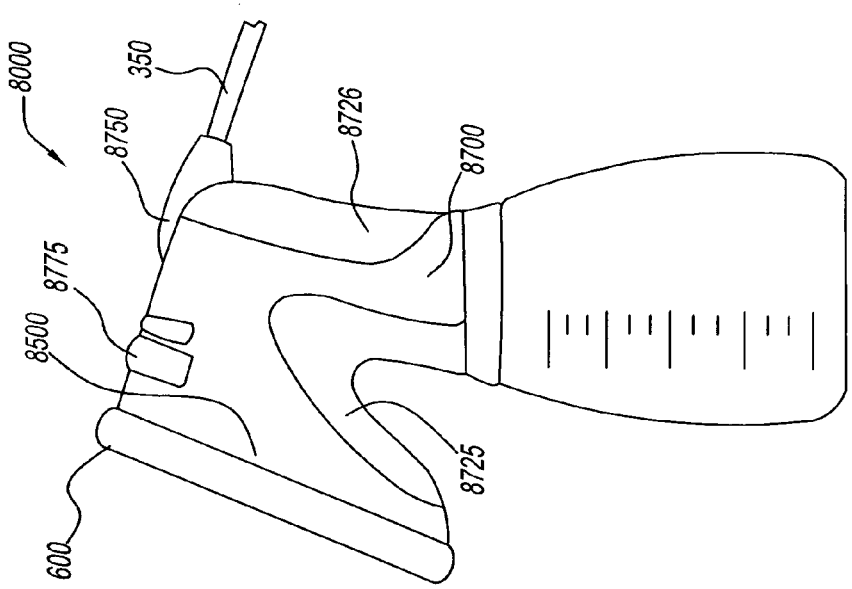
FIG. 28 is a plan view of another alternative embodiment of a breast cup of the present invention having gripping material on the handle.

Referring to FIG. 28, another alternative embodiment of the breast cup of the present invention is shown and generally represented by reference numeral 8000. Breast cup 8000 is also shown as an automatic pump but is usable with a manual pump, including a pumping mechanism that is affixed thereto such as the previously described embodiments. Breast cup 8000 is usable with insert 600. Breast cup 8000 has a funnel 8500 that is connected to a holder 8700. Holder 8700 has handle portions 8725, 8726, a pressure orifice 8750, and a pressure adjuster 8775. Handle portions 8725, 8726 are disposed on opposing sides of holder 8700 and facilitate grasping of the holder. Handle portions 8725, 8726 are preferably made of, or covered by, a material that facilitates gripping. Handle portions 8725, 8726 can include various textures, projections and/or embossments to sooth the user's hand during the pumping process.

The present invention having been thus described with particular reference to the preferred forms thereof, it will be obvious that various changes and modifications may be made therein without departing from the spirit and scope of the present invention as defined in the appended claims.

What is claimed is:

1. A manually operated breast pump, comprising:

a flexible insert for engaging a breast of a user, said flexible insert having a funnel-type shape;

a housing sealingly engaging said flexible insert;

a holder sealingly engaging said housing and sealingly engaging said flexible insert, providing an air volume in fluid isolation from breast milk passing through said flexible insert; and a pump mechanism sealingly engaging said holder, said pump mechanism having a handle extending in an upward direction from said holder, and a vacuum chamber, said vacuum chamber being in fluid communication with the air volume of said holder, said handle having a grip above a pivot point and a lower end below a pivot point, wherein said handle is adapted to move by exerting a pressure on said grip to move said grip toward said housing and the breast of the user to create a negative pressure communicated to said flexible insert and thereby on the user's breast and said handle is adapted to move said grip away from said housing to create a positive pressure communicated to said flexible insert and thereby on the user's breast, wherein said pump mechanism has a holder attachment having an inner volume that connects to said holder, an actuator having a planar portion and a connection portion perpendicular to said planar portion that attaches to said handle, and a chamber diaphragm that surrounds said connection portion of said actuator and connects to said holder attachment between said handle and said holder attachment defining a pump volume within said inner volume, wherein said inner volume is in fluid communication with said air volume and in fluid isolation from breast milk passing through said flexible insert, and wherein when said handle moves by exerting a pressure on said grip to move said grip toward said housing, said lower end exerts a pulling pressure in a direction opposite movement of said grip on said actuator to move said actuator within said inner volume with said lower end generating said negative pressure that is communicated to said flexible insert.

2. The manual breast pump of claim 1, further comprising a container that sealingly engages said holder and receives the expressed breast milk.

* * * * *